(12) United States Patent
Kinney et al.

(10) Patent No.: US 11,846,564 B2
(45) Date of Patent: Dec. 19, 2023

(54) OPTICAL SYSTEMS AND METHODS FOR LOCATING QUERY SYMBOLS IN A REFERENCE SEQUENCE

(71) Applicant: Western Digital Technologies, Inc., San Jose, CA (US)

(72) Inventors: Justin Kinney, San Jose, CA (US); Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 87 days.

(21) Appl. No.: 17/736,072

(22) Filed: May 3, 2022

(65) Prior Publication Data

US 2023/0358636 A1    Nov. 9, 2023

(51) Int. Cl.
*G01M 11/00* (2006.01)

(52) U.S. Cl.
CPC .... *G01M 11/3145* (2013.01); *G01M 11/3118* (2013.01)

(58) Field of Classification Search
CPC ............ G01M 11/3145; G01M 11/3118
See application file for complete search history.

(56) References Cited

U.S. PATENT DOCUMENTS 10,068,053 B2    9/2018 Kermani et al.
11,538,556 B2 *  12/2022 Rothberg ............... G06N 3/047
2011/0256631 A1* 10/2011 Tomaney ............. C12Q 1/6869
                                                            706/12
2020/0302224 A1    9/2020 Jaganathan et al.

FOREIGN PATENT DOCUMENTS

CN        210742122 U    6/2020

OTHER PUBLICATIONS

Alzubaidi et al.; "Biosensor based on microstructured optical fiber Bragg grating for DNA detection"; 2014 Fotonica AEIT Italian Conference on Photonics Technologies; May 2014; available at: https://ieeexplore.ieee.org/document/6843963.
(Continued)

*Primary Examiner* — Seung C Sohn
(74) *Attorney, Agent, or Firm* — Barry IP Law, P.C.

(57) ABSTRACT

A system includes at least one waveguide with optical interaction portions that represent a sequence of reference symbols based on the order of the optical interaction portions in the at least one waveguide. At least one light source sends photons of one or more predetermined wavelengths into the at least one waveguide representing a string of query symbols. A detector detects photons received from the at least one waveguide that result from optical interactions between photons sent into the at least one waveguide and one or more corresponding optical interaction portions with an interaction between photons and an optical interaction portion indicating a match between a query symbol and a reference symbol. An analyzer determines one or more respective relative locations of the one or more corresponding optical interaction portions indicating one or more relative locations of the string of query symbols in the reference sequence.

20 Claims, 13 Drawing Sheets

(56) References Cited

OTHER PUBLICATIONS

Candiani et al.; "Label-free DNA biosensor based on a peptide nucleic acid-functionalized microstructured optical fiber-Bragg grating"; J Biomed Opt.; May 10, 2013; available at: https://pubmed.ncbi.nlm.nih.gov/23698322/.

Delmdahl et al.; "Optics Fabrication: Fiber Bragg grating fabrication system is automated"; Fiber Optics; Feb. 16, 2016; available at: https://www.laserfocusworld.com/fiber-optics/article/16547082/optics-fabrication-fiber-bragg-grating-fabrication-system-is-automated.

Fujiki et al.; "GenAx: A Genome Sequencing Accelerator"; 2018 ACM/IEEE 45th Annual International Symposium on Computer Architecture (ISCA); Jun. 2018; available at: https://ieeexplore.ieee.org/document/8416819.

Keshmarzi et al.; "Spatially nonreciprocal Bragg gratings based on surface plasmons"; Applied Physics Letters; Nov. 14, 2014; available at: https://aip.scitation.org/doi/10.1063/1.4901818.

Kurtaran et al.; "The modelling of Fiber Bragg Grating"; Optical and Quantum Electronics 39; Sep. 8, 2007; available at: https://link.springer.com/article/10.1007/s11082-007-9117-1.

Mak et al.; "Mirrors made of a single atomic layer"; Nature; Apr. 12, 2018; available at: https://www.nature.com/articles/d41586-018-04089-1#:~:text=Researchers%20have%20demonstrated%20that%20atomically,nanophotonics%2C%20optoelectronics%20and%20quantum%20optics.

Maleki et al.; "High-speed all-optical DNA local sequence alignment based on a three-dimensional artificial neural network"; Journal of the Optical Society of America A; Jun. 22, 2014; available at: https://opg.optica.org/josaa/abstract.cfm?uri=josaa-34-7-1173.

Mozafari et al.; "Speeding up DNA sequence alignment by optical correlator"; Optics & Laser Technology; Dec. 2018; available at: https://www.sciencedirect.com/science/article/abs/pii/S003039921731575X.

Najam et al.; "Pattern Matching for DNA Sequencing Data Using Multiple Bloom Filters"; BioMed Research International; Apr. 14, 2019; available at: https://www.hindawi.com/journals/bmri/2019/7074387/.

Rui et al.; "A subradiant optical mirror formed by a single structured atomic layer"; Nature; Jul. 15, 2020; available at: https://www.nature.com/articles/s41586-020-2463-x.

Wikipedia; "Fiber Bragg grating Theory"; accessed on May 3, 2022; available at: https://en.wikipedia.org/wiki/Fiber_Bragg_grating#Theory.

Yuan et al.; "High speed single photon detection in the near-infrared"; Applied Physics Letter; Jul. 29, 2007; available at: https://arxiv.org/abs/0707.4307.

\* cited by examiner

US 11,846,564 B2

OPTICAL SYSTEMS AND METHODS FOR LOCATING QUERY SYMBOLS IN A REFERENCE SEQUENCE

BACKGROUND

Limitations in current DNA (deoxyribonucleic acid) and RNA (ribonucleic acid) sample handling lead to sample strings or portions of a sample genome having a generally unknown location in the sample genome. The sample strings must then be sequenced or put back into their locations in the sample genome. The two main types of genome sequencing are de novo sequencing and reference-aligned sequencing. Referenced-aligned sequencing uses a reference genome to locate the sample strings within the sample genome. De novo sequencing, on the other hand, does not typically use a reference genome, but instead compares sample strings to each other to locate the sample strings within the sample genome.

Sequencing sample genomes generally requires a long processing time that can take hundreds to thousands of processor hours to compare the sample genomes to the reference genome. In this regard, the human reference genome H38 is a sequence of reference symbols that is approximately 3.2 billion symbols long including reference symbols A, C, G, and T for the four types of base pairs found in a DNA molecule. Similarly, locating other types of strings of query symbols within a much longer reference sequence in other fields such as data analytics can also take a significant number of processor hours.

Current systems and methods for locating or sequencing strings of query symbols in large sequences of reference symbols may include different arrangements of, for example, Content Addressable Memory (CAM) or Ternary CAM (TCAM) for performing different phases of exact matching and/or approximate matching. However, the computing efficiency of such systems and methods still needs to improve by orders of magnitude to shorten the time to sequence or locate strings of query symbols in long sequences of reference symbols. Accordingly, there is a need to improve the processing efficiency of systems and methods that locate or sequence strings of query symbols within large sequences of reference symbols.

BRIEF DESCRIPTION OF THE DRAWINGS

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

DETAILED DESCRIPTION

In the following detailed description, numerous specific details are set forth to provide a full understanding of the present disclosure. It will be apparent, however, to one of ordinary skill in the art that the various embodiments disclosed may be practiced without some of these specific details. In other instances, well-known structures and techniques have not been shown in detail to avoid unnecessarily obscuring the various embodiments.

Example System Overview

Figure 1:
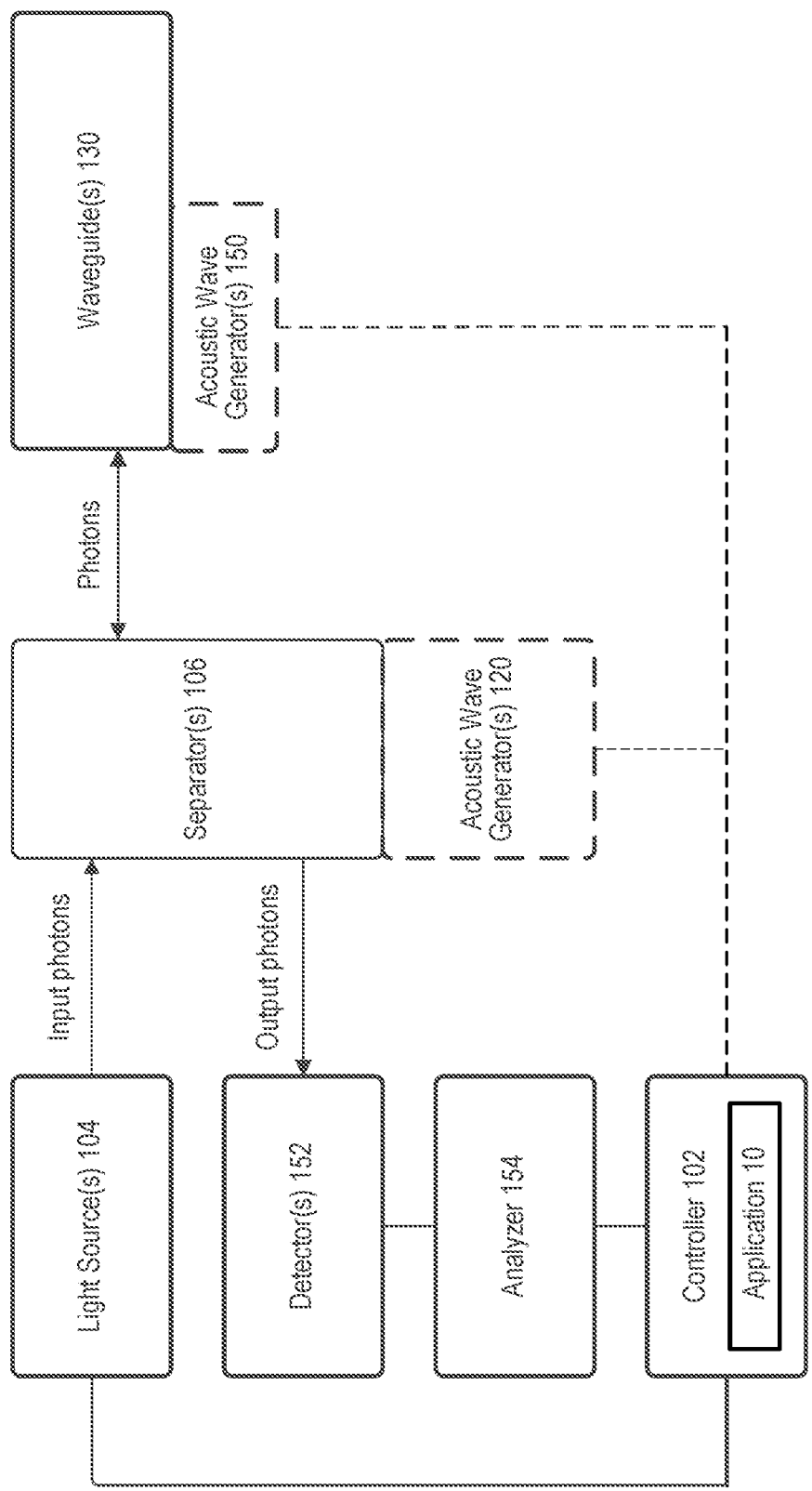
FIG. 1 is a block diagram of a system for locating query symbols within a reference sequence using at least one waveguide according to one or more embodiments.

FIG. 1 is a block diagram of system 100 for locating query symbols within a reference sequence using one or more waveguides 130 according to one or more embodiments. System 100 may be used, for example, to locate one or more relative locations of a string of query symbols within a sequence of reference symbols. In some implementations, the string of query symbols can include a sample genome to be located or sequenced within a reference genome, such as the human genome. In other implementations, the string of query symbols may represent data to be located or sequenced within a larger sequence of data to identify patterns, such as within an encrypted code or for data analytics.

For ease of description, the examples in this disclosure will be described in the context of DNA (deoxyribonucleic acid) sequencing. However, the embodiments of the present disclosure are not limited to DNA sequencing and can be generally applied to any nucleic acid-based sequencing including RNA (ribonucleic acid) sequencing or any other application for locating one or more query symbols within a reference sequence.

In the example of FIG. 1, controller 102 controls one or more light sources 104 and optionally controls acoustic wave generators 120 and/or 150 in implementations where acoustic waves are propagated into one or more separators 106 and/or one or more waveguides 130. Controller 102 also communicates with analyzer 154, which receives signals from one or more detectors 152 for determining one or more relative locations of a query symbol or a string of query symbols in a reference sequence.

Controller 102 can include, for example, hard-wired logic, analog circuitry and/or a combination thereof. In some implementations, controller 102 can include one or more Application Specific Integrated Controllers (ASICs), microcontrollers, Digital Signal Processors (DSPs), Field Programmable Gate Arrays (FPGAs), and/or a combination thereof. In some implementations, controller 102 can include one or more Systems on a Chip (SoCs). In other implementations, controller 102 can include a computer, such as a desktop, a laptop, or a server. In some implementations, controller 102 and analyzer 154 may be combined into a single device.

As shown in FIG. 1, controller 102 stores application 10 in a memory of controller 102. Application 10 can include computer-executable instructions that can be executed by, for example, one or more processors of controller 102, such as a Central Processing Unit (CPU) to control devices in system 100, such as light source(s) 104, analyzer 154, and/or acoustic wave generators. In some implementations, application 10 can cause system 100 to perform a process for locating one or more query symbols in a reference sequence, such as the example process of FIG. 14 discussed below.

Light source(s) 104 can include, for example, one or more lasers configured to supply photons of a predetermined wavelength. As discussed in more detail below, each light source 104 can emit photons of a particular wavelength representing a different query symbol. The wavelengths can include ultraviolet, visible, and/or infrared wavelengths or frequencies.

As discussed in more detail below with reference to FIGS. 9 to 11, separator or separators 106 can include, for example, one or more beam splitters, acousto-optic deflectors, and/or dichroic mirrors. Separator(s) 106 provide a path for input photons from lights source(s) 104 to enter one or more waveguides 130 and for output photons exiting from the one or more waveguides 130 to be detected by detector(s) 152. The output photons exiting from the one or more waveguides 130 result from optical interactions between input photons entering the one or more waveguides 130 and one or more optical interaction portions within the one or more waveguides 130.

Waveguide(s) 130 can include, for example, optical fiber waveguides, planar waveguides, or other waveguides that include optical interaction portions representing a sequence of reference symbols. As discussed in more detail below, each optical interaction portion represents a reference symbol and an optical interaction between input photons of a predetermined wavelength and the optical interaction portion represents a match between the query symbol represented by the predetermined wavelength and the reference symbol represented by the optical interaction portion. The optical interaction portions can include, for example, non-reciprocal gratings (e.g., nonreciprocal Bragg gratings) that reflect light of the predetermined wavelength from only one direction, acousto-optic gratings that temporarily reflect light of the predetermined wavelength when modified by an acoustic wave, or luminescent material portions that when excited by light of a first predetermined wavelength emit photons of a second predetermined wavelength.

Acoustic wave generator(s) 150 are used to propagate an acoustic wave along one or more wave guides 130 in implementations where the one or more waveguides 130 include acousto-optic gratings. In some implementations, acoustic wave generator(s) 150 can include a driver or amplifier controlled by controller 102 and a transducer, such as a piezoelectric transducer for converting a signal from the driver or amplifier into an acoustic wave. The acoustic wave generated by the acoustic wave generator then travels along the waveguide 130 to temporarily modify the acousto-optic gratings in the waveguide to enable reflection of the respective predetermined wavelengths that the acousto-optic gratings have been tuned to reflect, which corresponds to the reference symbol represented by the acousto-optic grating.

Acoustic wave generator(s) 120 are used to propagate an acoustic wave into one or more acousto-optic deflectors in implementations where separator(s) include one or more acousto-optic deflectors and the one or more waveguides 130 include luminescent material portions. In some implementations, acoustic wave generator(s) 120 can include a driver or amplifier controlled by controller 102 and a transducer, such as a piezoelectric transducer for converting a signal from the driver or amplifier into an acoustic wave. The acoustic wave generated by the acoustic wave generator then travels into a body of the acousto-optic deflector to temporarily modify the body of the deflector, which may include a crystal, to reflect input photons of a first predetermined wavelength. After the acoustic wave no longer modifies the structure of the body of the deflector, output photons of a second predetermined wavelength that may result from optical interactions with luminescent material portions in one or more waveguides 130 can pass through the body of the deflector to one or more detectors 152.

Detector(s) 152 can include one or more devices that convert photons received from separator(s) 106 into an output signal, such as an output voltage that is read by analyzer 154. In some implementations detector(s) 152 can include, for example, one or more avalanche photodetectors or photodiodes, or another type of detector that can detect photons and provide an output to analyzer 154 indicating a level or number of photons detected at a particular time.

Analyzer 154 can include, for example, one or more ASICs, microcontrollers, DSPs, FPGAs, and/or a combination thereof. In some implementations, analyzer 154 can include one or more SoCs. In other implementations, analyzer 154 can include a computer, such as a desktop, a laptop, or a server. As noted above, controller 102 and analyzer 154 may be combined in some implementations into a single device.

Analyzer 154 determines one or more relative locations of a query symbol or a string of query symbols represented by different wavelengths of detected photons in a reference sequence represented by the order of optical interaction portions in waveguide(s) 130. In some implementations, analyzer 154 can determine one or more respective locations of one or more optical interaction portions in waveguide(s) 130 identified as peaks (e.g., a peak voltage or greater than a threshold value) in the signal received from detector(s) 152. The determined relative locations can include, for example, indices of where the input query symbols represented by the input photons of a predetermined wavelength match the reference symbols in the reference sequence represented by the optical interaction portions. In some implementations, and as discussed in more detail below with reference to FIGS. 12 and 13, an index for the relative location of an optical interaction portion can be determined based on an approximate photon travel time between when input photons enter the waveguide(s) and when the output photons resulting from an optical interaction with the optical interaction portion are detected by detector(s) 152.

As discussed in more detail below, the use of optical waveguides to identify relative locations of query symbols in a reference sequence can significantly decrease the processing time to identify the relative locations as compared to conventional systems and methods. This improvement is more noticeable as the difference between the length of the string of query symbols and the reference sequence increases. The processing efficiency of the disclosed systems and methods can generally be further improved by performing more processing in an optical domain as opposed to an electrical domain.

Figure 5A:
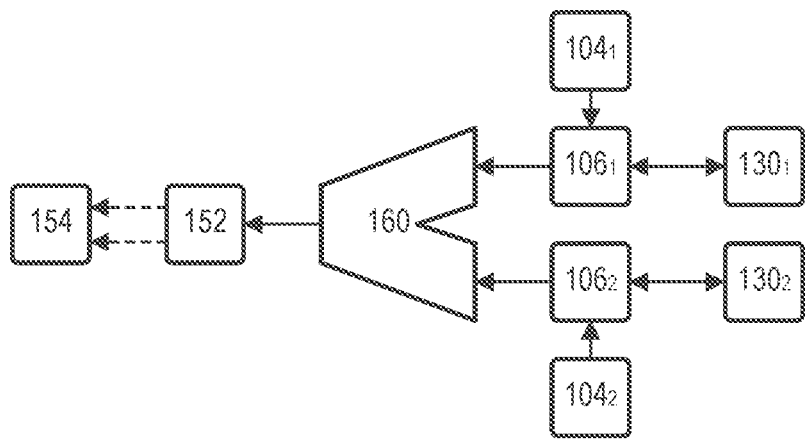
FIG. 5A depicts an arrangement of a system including a single detector and multiple waveguides according to one or more embodiments.
Figure 5B:
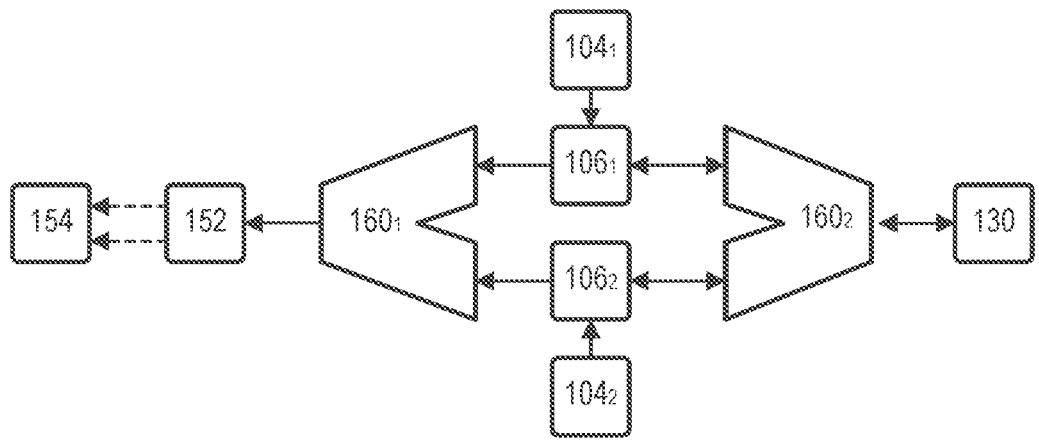
FIG. 5B depicts an arrangement of a system including a single detector and a single waveguide according to one or more embodiments.
Figure 5C:
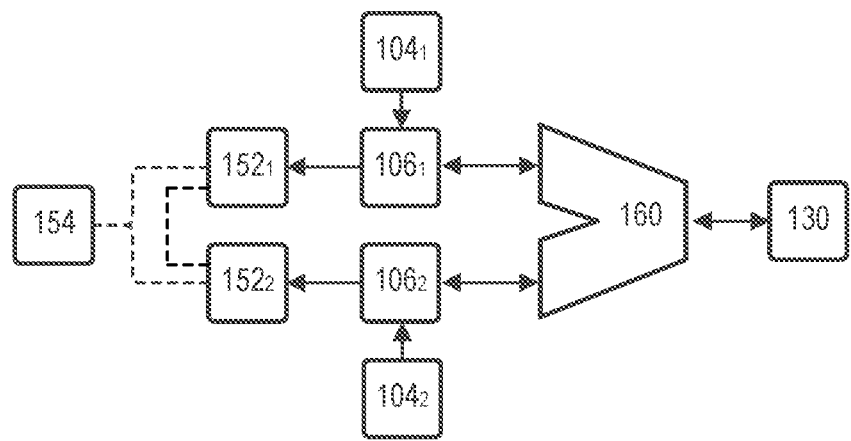
FIG. 5C depicts an arrangement of a system including a single waveguide and multiple detectors according to one or more embodiments.

Those of ordinary skill in the art with reference to the present disclosure will appreciate that other implementations of system 100 can include different components or a different arrangement of components than shown in FIG. 1. For example, other implementations of system 100 may include one or more couplers as shown in FIGS. 5A to 5C to combine or decouple light paths of photons with different wavelengths.

Waveguide Examples

Figure 2A:
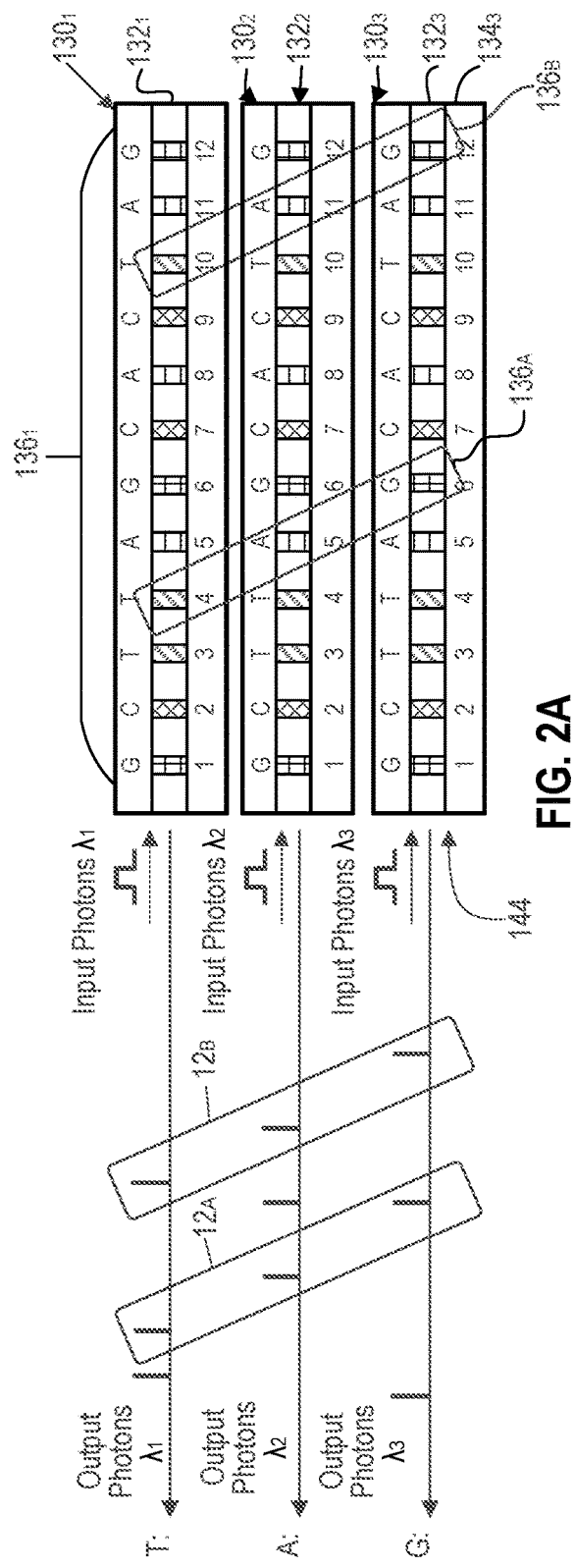
FIG. 2A illustrates a concurrent input of photons with different predetermined wavelengths into respective waveguides according to one or more embodiments.

FIG. 2A illustrates a concurrent input of photons with different predetermined wavelengths into respective waveguides 130 according to one or more embodiments. As shown in FIG. 2A, three pulses of photons with three different predetermined wavelengths (i.e., $\lambda_1$, $\lambda_2$, and $\lambda_3$) are sent into three corresponding waveguides $130_1$, $130_2$, and $130_3$. Each of the three different predetermined wavelengths represents a different query symbol. In the example of FIG. 2A, wavelength $\lambda_1$ represents query symbol T for the base thymine, $\lambda_2$ represents query symbol A for the base adenine, and $\lambda_3$ represents query symbol G for the base guanine. Together, the three pulses of photons of different wavelengths represent a string of query symbols TAG.

The pulses for the three different wavelengths are concurrently input or sent into respective waveguides $130_1$, $130_2$, and $130_3$, which each includes the same set of optical interaction portions, such as optical interaction portions $136_1$ in core $132_1$ of waveguide $130_1$. The waveguides $130_1$, $130_2$, and $130_3$ in FIG. 2A are shown as optical fibers that include a core 132 for carrying the photons and is surrounded by a cladding with a lower refractive index and an outer coating to protect the core.

As shown in FIG. 2A, each of the optical interaction portions in optical interaction portions $136_1$ represents a reference symbol (i.e., A, C, G, or T), which is shown above core $132_1$ for the purposes of illustration. The order of the optical interaction portions in the waveguide represents a sequence of the reference symbols. In the example of FIG. 2A, each of waveguides $130_1$, $130_2$, and $130_3$ represent the reference sequence of GCTTAGCACTAG, which may, for example, form part of the human reference genome. Those of ordinary skill in the art will appreciate with reference to the present disclosure that the sequences of reference symbols can be significantly longer than the example used for FIG. 2A, which is generally shorter for purposes of illustration.

Each optical interaction portion 136 is located at a relative location in the waveguide, which is indicated by an index (i.e., indices 1 to 12 in FIG. 2A) shown below the core for purposes of illustration. As discussed in more detail below, the relative locations or indices for optical interaction portions that optically interact with input photons of a predetermined wavelength can be determined by analyzer 154 to determine one or more relative locations in the reference sequence of a query symbol represented by the predetermined wavelength or determine one or more relative locations of a string of query symbols represented by a set of predetermined wavelengths.

In the example of FIG. 2A, the string of query symbols is TAG, which is represented by predetermined wavelengths Ai, $\lambda_2$, and $\lambda_3$, respectively. A pulse of photons of predetermined wavelength Ai representing query symbol T is sent into waveguide $130_1$ that optically interacts with corresponding optical interaction portions representing reference symbol T at indices 3, 4, and 10 in core $132_1$. A pulse of photons of predetermined wavelength $\lambda_2$ representing query symbol A is sent into waveguide $130_2$ that optically interacts with corresponding optical interaction portions representing reference symbol A at indices 5, 8, and 11 in core $132_2$. A pulse of photons of predetermined wavelength $\lambda_3$ representing query symbol G is sent into waveguide $130_3$ that optically interacts with corresponding optical interaction portions representing reference symbol G at indices 1, 6, and 12 in core 1323.

Output photons exit each waveguide that result from optical interactions with the corresponding optical interaction portions that match the predetermined wavelength of the input photons sent into the waveguide. In FIG. 2A, each waveguide has three peaks of output photons corresponding to the relative locations of the matching optical interaction portions for the predetermined wavelength of the pulse of input photons. In this example, the output photons may be reflected out of the waveguide by the corresponding or matching optical interaction portions. In implementations where the optical interaction portions reflect the photons of the predetermined wavelength, such as with nonreciprocal Bragg gratings or acousto-optic gratings, the optical interaction portions can be tuned to only reflect photons of the predetermined wavelength and to let photons of different wavelengths to continue to travel through the waveguide. In addition, such reflective optical interaction portions are further tuned to reflect increasing amounts of photons of the predetermined wavelength the farther they are located from entry sides 144 of waveguides 130 where the pulses of photons enter waveguides 130. In this way, the amount of output photons that exit the waveguide 130 for each corresponding or matching optical interaction portion is approximately the same regardless of the location of the optical interaction portion along the waveguide 130.

One or more detectors (e.g., detector(s) 152 in FIG. 1) can detect the photons exiting waveguides 130 and convert the detected photons or peaks of photons received from waveguides 130 into a signal. An analyzer (e.g., analyzer 154 in FIG. 1) can then determine the locations of the query string TAG within the reference sequence GCTTAGCACTAG based on a difference in time between the pulses of input photons being sent into waveguides 130 and when the reflected output photons or peaks of output photons are detected. As shown in FIG. 2A, the groups of input photons identified in boxes $12_A$ and $12_B$ correspond to the groups of optical interaction portions identified in boxes $136_A$ and 1368. As discussed in more detail below, the analyzer can determine the relative locations or indices for the corresponding optical interaction portions for the matching string of query symbols.

Figure 6:
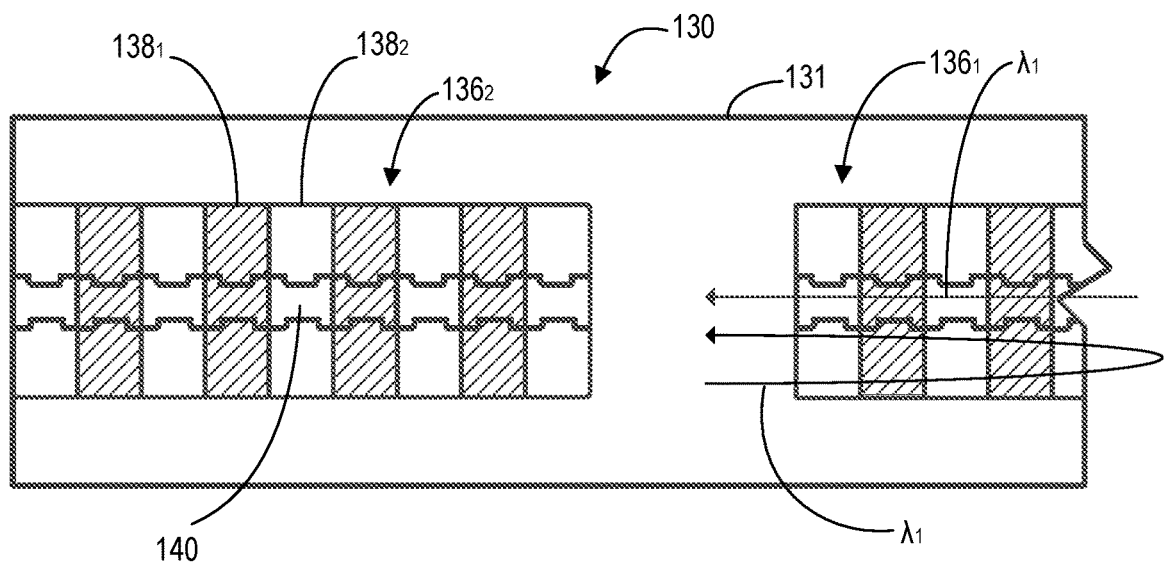
FIG. 6 depicts nonreciprocal gratings in a planar waveguide according to one or more embodiments.

Those of ordinary skill in the art will appreciate with reference to the present disclosure that other implementations may differ from the example shown in FIG. 2A. For example, other implementations may not use optical fibers for waveguides 130, but may instead use a different type of waveguide, such as a planar waveguide as shown in the example of FIG. 6 discussed below. As another example variation, the number of query symbols or pulses of input photons of the predetermined wavelengths may differ or a single waveguide may be used instead of a separate waveguide for each predetermined wavelength.

Figure 2C:
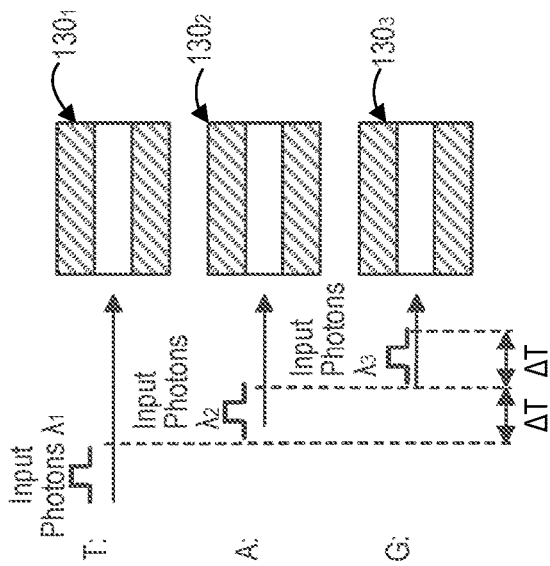
FIG. 2C illustrates delaying the input of photons into the waveguides of FIG. 2A according to one or more embodiments.
Figure 2B:
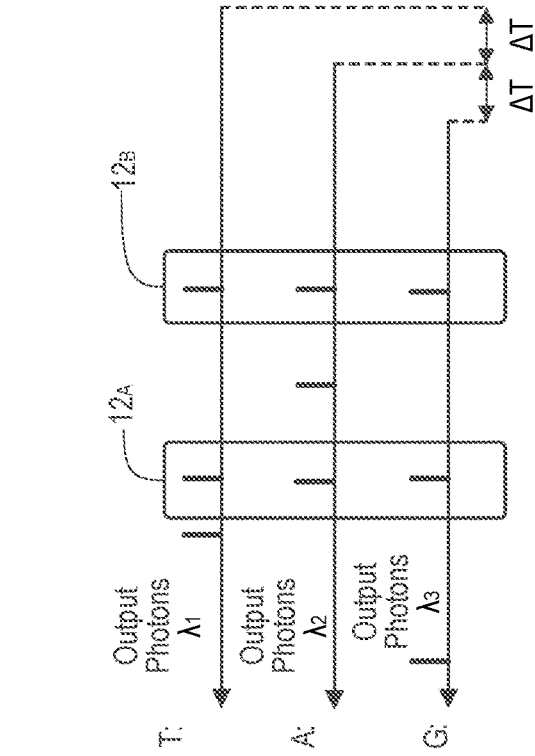
FIG. 2B illustrates delaying the detection of photons output from the waveguides of FIG. 2A or the delaying of signals output from a detector according to one or more embodiments.

FIG. 2B illustrates delaying the detection of photons output from waveguides 130 or the delaying of signals output by one or more detectors according to one or more embodiments. The delaying can be performed, for example, by using separate detectors that are offset by a predetermined period of time corresponding to the distance between adjacent optical interaction portions in waveguides 130. In another example implementation, the detected outputs from one or more detectors can be buffered for up to the square of the number of query symbols in the query string to shift the detected outputs by one position relative to the previous query symbol in the query string.

In the example of FIG. 2B, the output photons are approximately aligned in time by delaying the output resulting from the individual waveguides 130. In particular, the output from waveguide $130_2$ for predetermined wavelength $\lambda_2$ is delayed by $\Delta T$ and the output from waveguide $130_3$ for predetermined wavelength $\lambda_2$ is delayed by $2\Delta T$ so that the groups of detected photons $12_A$ and $12_B$ temporally overlap to indicate a match of the TAG query string in the reference sequence represented by the optical interaction portions. In the example of FIGS. 2A and 2B, the detected output from each waveguide 130 after the first waveguide $130_1$ for the first query symbol in the query string (i.e., T) is delayed by an additional time period of $\Delta T$.

The time period $\Delta T$ equals twice the pitch of the optical interaction portions (i.e., the distance from the start of one optical interaction portion to the start of the next optical interaction portion) in waveguides 130 divided by the speed of light in cores 132, which is the constant c for the speed of light in a vacuum that is scaled or reduced by the index of refraction for the cores 132. Equation 1 below represents an expression for $\Delta T$:

$$\Delta T = \frac{2W}{(c/n)} \quad \text{Eq. 1}$$

where W is the pitch between optical interaction portions, c is the speed of light in a vacuum, and n is the index of refraction for the cores 132 to account for the material of the core and changes to the material at the optical interaction portions.

FIG. 2C illustrates delaying the input of photons into the waveguides 130 of FIG. 2A according to one or more embodiments. Instead of delaying the detection of the output of the photons as discussed above for FIG. 2B, the input of the pulses of photons for the different predetermined wavelengths into entry side 144 of waveguides 130 can be delayed by $\Delta T$ from the previous pulse of photons for the previous query symbol in the query string. As shown in FIG. 2C, the pulse of input photons for $\lambda_2$ is delayed by $\Delta T$ from the pulse of input photons for $\lambda_1$, and the pulse of input photons for $\lambda_3$ is delayed by $\Delta T$ from the pulse of input photons for $\lambda_2$.

The resulting output for the locations in waveguides 130 where the string of query symbols for $\lambda_1$, $\lambda_2$, and $\lambda_3$ (i.e., the query symbol string TAG) matches the reference symbols represented by the optical interaction portions for $\lambda_1$, $\lambda_2$, and $\lambda_3$ is temporally aligned. A detector may then indicate a greater signal level (e.g., voltage) with a spike or peak in the signal that the analyzer can identify as a match between the string of query symbols and the reference symbols. As discussed in more detail below with reference to FIGS. 12 and 13, the time at which the spikes or peaks in the signal are detected can correspond to the relative locations (e.g., indices) of the matching optical interaction portions in the waveguides. The travel time of the first symbol or predetermined wavelength (i.e., Ai for query symbol T) in the query string can be used to determine the relative location or start of the reference symbols in the reference sequence that match the string of query symbols.

Figure 2D:
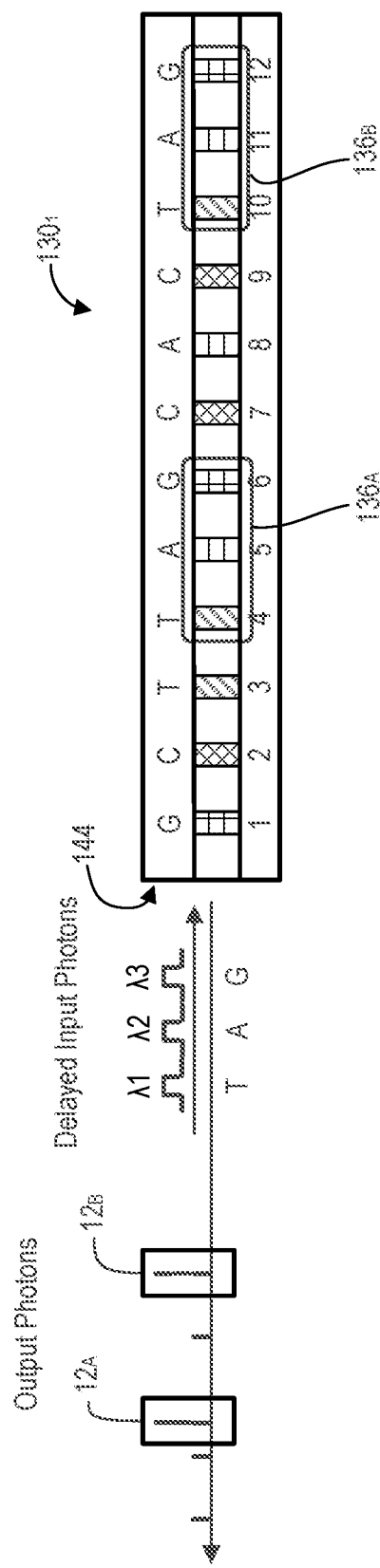
FIG. 2D illustrates delaying the input of photons into a single waveguide according to one or more embodiments.

FIG. 2D illustrates delaying the input of pulses of photons into a single waveguide $130_1$ according to one or more embodiments. As shown in FIG. 2D, pulses of photons having predetermined wavelengths of $\lambda_1$, $\lambda_2$, and $\lambda_3$ are sequentially input or sent into waveguide $130_1$ to represent the string of query symbols TAG. Output photons exiting waveguide $130_1$ are approximately aligned and grouped at the locations identified by boxes $12_A$ and $12_B$ indicating locations where the string of query symbols matches the reference symbols represented by the optical interaction portions identified as $136_A$ and $136_B$. In some implementations, the analyzer may then determine indices 4 and 10 as the relative locations of the string of query symbols in the reference sequence represented by the optical interaction portions of waveguide $130_1$.

Figure 3A:
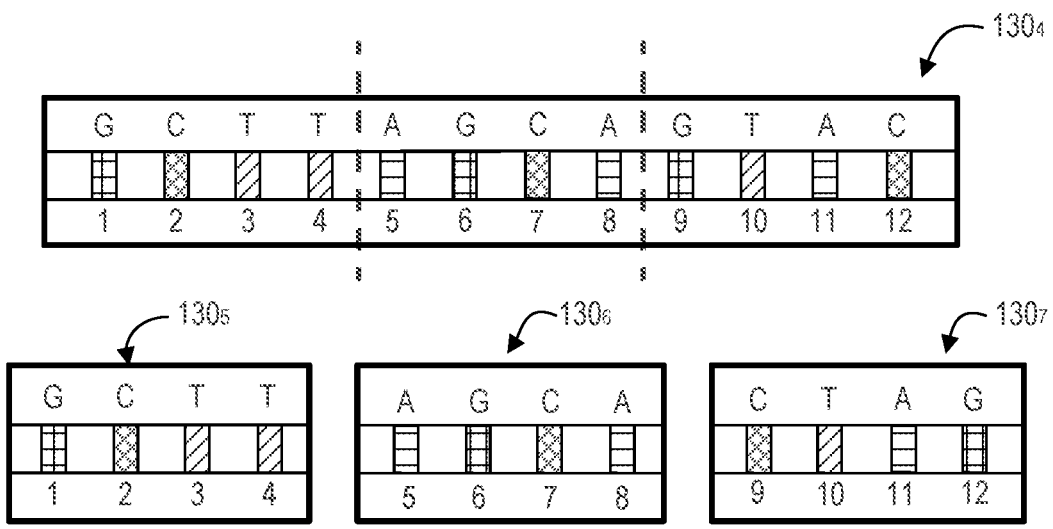
FIG. 3A depicts a waveguide including optical interaction portions representing a reference sequence and partitioning the optical interaction portions into three shorter waveguides according to one or more embodiments.

FIG. 3A depicts waveguide $130_4$ including optical interaction portions representing a reference sequence and partitioning the optical interaction portions into three waveguides $130_5$, $130_6$, and $130_7$ according to one or more embodiments. By partitioning a waveguide into smaller pieces, it is possible to use shorter waveguides. In some implementations, the same predetermined wavelength or set of predetermined wavelengths (i.e., the same query string) can be sent into each of the shorter waveguides $130_5$, $130_6$, and $130_7$, which corresponds to searching three smaller sections of the reference sequence represented by the optical interaction portions of the longer waveguide $130_4$. The use of shorter sections of a longer waveguide as in the example of FIG. 3A can be useful in cases where the optical interaction portions may have less scalability in the number of output photons that can be reflected or otherwise sent back for detection or where the sensitivity of the detector requires a greater number of output photons for detection. As another example, the use of shorter sections of a longer waveguide as in FIG. 3A can be useful in cases where an acoustic wave is used by the optical interaction portions so that the acoustic wave has enough power to modify the structure of all of the optical interaction portions along the waveguide.

Figure 3B:
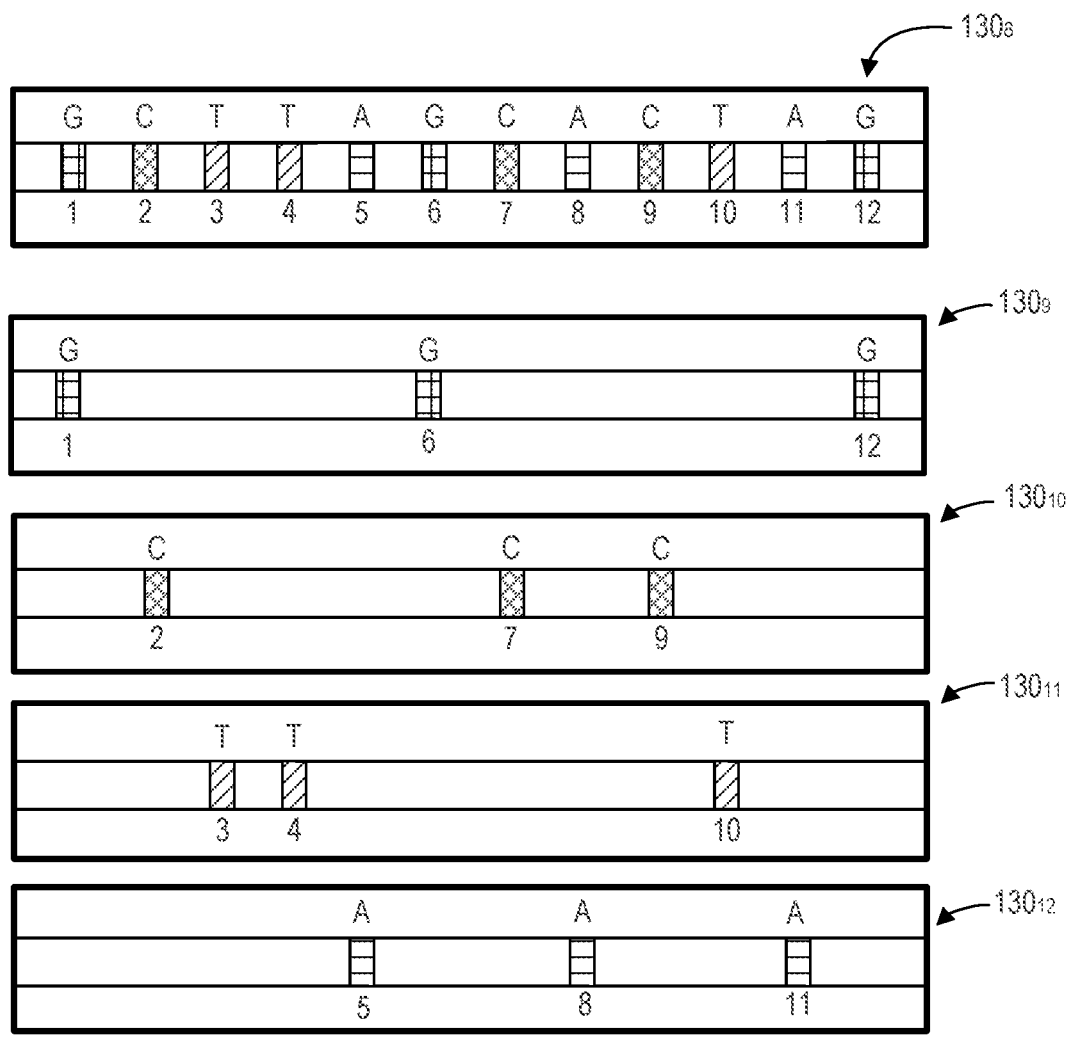
FIG. 3B depicts a waveguide including optical interaction portions representing a reference sequence and distributing the optical interaction portions by corresponding wavelengths across four waveguides according to one or more embodiments.

FIG. 3B depicts a waveguide $130_8$ including optical interaction portions representing a reference sequence and the distribution of the optical interaction portions by respective wavelengths across four waveguides according to one or more embodiments. As shown in FIG. 3B, each of the four reference symbols G, C, T, and A have their own waveguide with waveguide $130_9$ representing the locations of reference symbol G at indices 1, 6, and 12 in the sequence, waveguide $130_{10}$ representing the locations of reference symbol C at indices 2, 7, and 9 in the sequence, waveguide $130_{11}$ representing the locations of reference symbol T at indices 3, 4, and 10 in the sequence, and waveguide $130_{12}$ representing the locations of reference symbol A at indices 5, 8, and 11 in the sequence.

A pulse of photons with the predetermined wavelength corresponding to the reference symbol for each of waveguides $130_9$, $130_{10}$, $130_{11}$, and $130_{12}$ can be sent into their respective waveguides 130. The time between the photons entering the waveguide and the detection of the photons exiting the waveguide (i.e., the photon travel time) can be used to determine the relative locations of the matching reference symbols in the reference sequence. Similar to the example of shorter waveguides in FIG. 3A, using waveguides with less optical interaction portions for different predetermined wavelengths may improve the detection of photons exiting the waveguides due to less unintentional interference caused by other optical interaction portions corresponding to different predetermined wavelengths. In some implementations, the distribution of optical interaction portions by respective wavelengths into different waveguides as in the example of FIG. 3B can facilitate or simplify the manufacture of the waveguides, such as where the same luminescent material can be deposited into one waveguide for each of the different luminescent materials used in the different optical interaction portions corresponding to the different predetermined wavelengths.

System Arrangement Examples

Figure 4A:
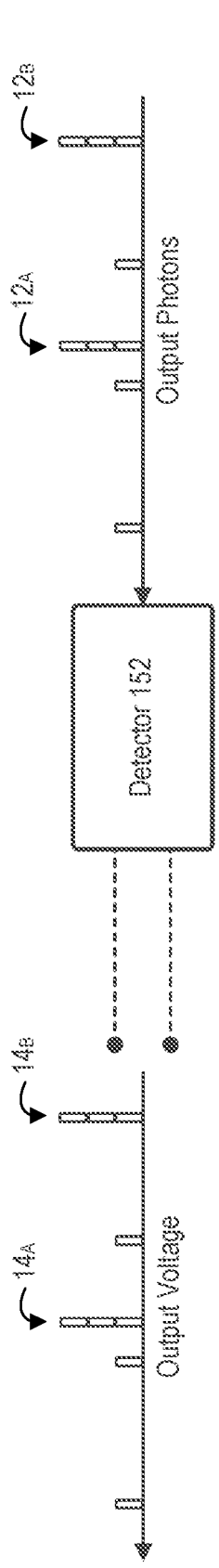
FIG. 4A depicts the conversion of photons output from a single waveguide into output voltages by a detector according to one or more embodiments.

FIG. 4A depicts the conversion of photons output from a single waveguide into output voltages by detector 152 according to one or more embodiments. As shown in FIG. 4A, aligned groups $12_A$ and $12_B$ of output photons are converted into peak voltages $14_A$ and $14_B$, respectively. The output photons may come from a single waveguide, such as waveguide $130_1$ in FIG. 2D, where pulses of input photons are staggered to result in aligned output photons representing matches of the query string in the reference sequence.

The aligned output photons are summed by the detector to generate a proportional voltage to the sum of the photons at a given time or processing cycle of the detector. In implementations where each optical interaction portion provides an approximately equal number of photons exiting the waveguide for its predetermined wavelength, the analyzer may have a threshold voltage set based on the number of query symbols so that voltages at or greater than the threshold voltage indicate a match between the string of query symbols and the reference symbols in the reference sequence. In some implementations, the detector may not be sensitive to different wavelengths and the analyzer may only need to consider the level of the signal received from the detector to determine whether the signal indicates a match with the query string. In this regard, the amount of output photons detected for a match or the resulting signal level for a match can be determined with testing of the system.

Figure 4B:
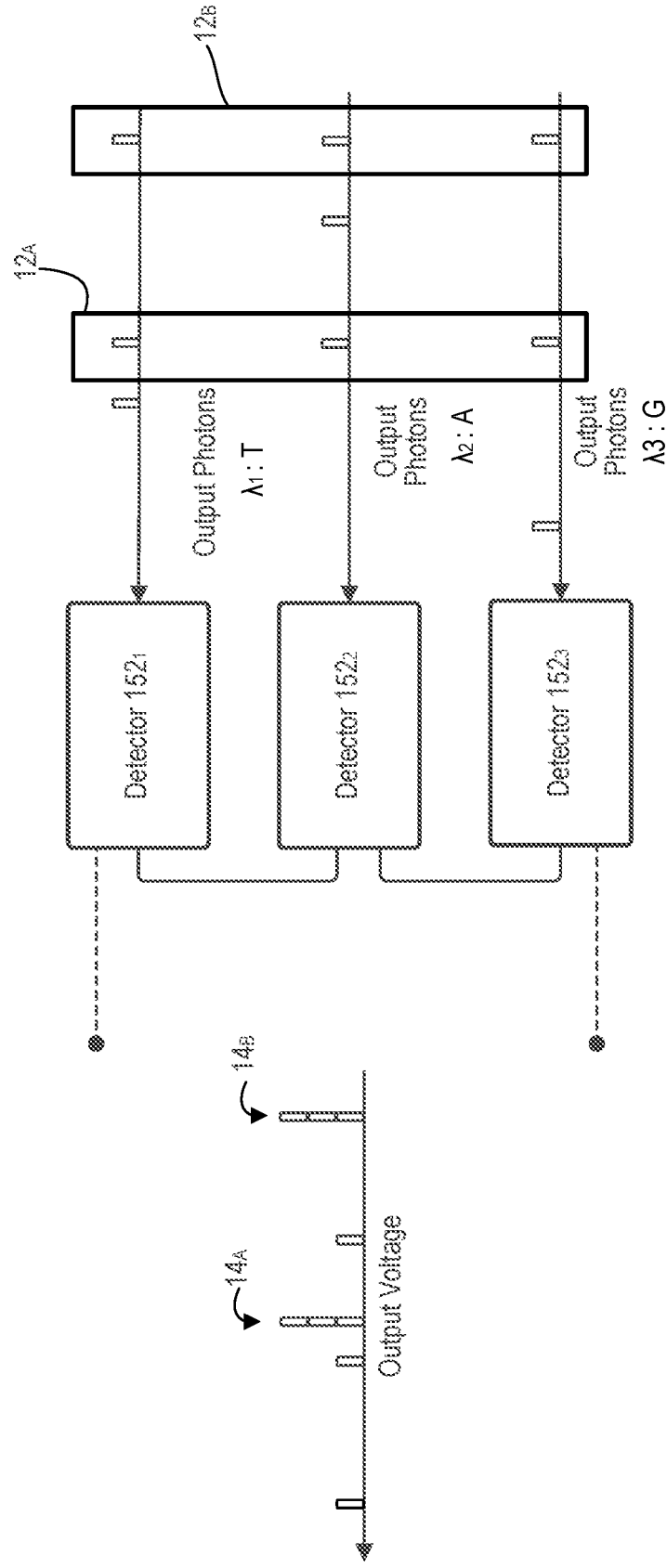
FIG. 4B depicts the conversion of photons output from three waveguides into output voltages by three detectors according to one or more embodiments.

FIG. 4B depicts the conversion of photons output from three waveguides into output voltages by three detectors according to one or more embodiments. As shown in FIG. 4B, three sets of output photons for predetermined wavelengths $\lambda_1$, $\lambda_2$, and $\lambda_3$, respectively, are received by respective detectors $152_1$, $152_2$, and $152_3$. Each detector 152 in the example of FIG. 4B detects photons for a different symbol. The output signal is then supplied as a voltage from the detectors 152 with peak voltages at $14_A$ and $14_B$ indicating matches between the string of query symbols TAG and reference symbols in the reference sequence.

As noted above with reference to system 100 of FIG. 1, detectors 152 can include, for example, avalanche photodetectors or photodiodes. In some implementations, an InGaAs avalanche photodetector may be used that can detect single photons in a near infrared spectrum. Other implementations may use, for example, a Si avalanche photodetector that can detect photons with wavelengths ranging from 850 nanometers (nm) to 1700 nm. Other examples of detectors may not detect individual photons but can detect relative amounts of photons within a response time or detection cycle. Certain avalanche photodetectors can have a high-speed response of up to 1 Gigahertz (GHz). The pitch and sizing of the optical interaction portions in the waveguide may therefore be sized to enable the detector to distinguish the timing between when output photons are received from adjacent optical interaction portions. In addition, to avoid losing information, photons from individual optical interaction portions should occupy a time of nanoseconds or longer given a bandwidth of 1 GHz.

FIG. 5A depicts an arrangement of system 100 including a single detector 152 and waveguides $130_1$ and $130_2$ according to one or more embodiments. Each of waveguides $130_1$ and $130_2$ is fed photons from its own light source $104_1$ and $104_2$, respectively. The photons from light sources $104_1$ and $104_2$ can have two different predetermined wavelengths representing two query symbols. The photons travel into either separator $106_1$ or $106_2$ and are directed into waveguide $130_1$ or $130_2$.

The photons leaving waveguides $130_1$ and $130_2$ exit into separators $106_1$ or $106_2$ and are directed into coupler 160, which combines the photons into a single light path into detector 152. Although the example of coupler 160 shows the combination of two light paths, other couplers can be used to combine more light paths, such as four light paths for each of the four query symbols discussed above. For its part, detector 152 converts the photons received from coupler 160 into an electrical signal provided to analyzer 154, which determines relative locations of the optical interaction portions in waveguides $130_1$ and $130_2$ that indicate a match between the string of query symbols and the reference symbols represented by the optical interaction portions.

FIG. 5B depicts an arrangement of system 100 including a single detector 152 and a single waveguide 130 according to one or more embodiments. Waveguide 130 is fed input photons from light sources $104_1$ and $104_2$ that are directed to coupler $160_2$, which combines the light paths before the input photons enter waveguide 130. Each of light sources $104_1$ and $104_2$ may emit photons of different predetermined wavelengths representing two different query symbols. The timing of the emission of the photons may be controlled by a controller (e.g., controller 102 in FIG. 1) to provide a reverse order of the string of query symbols separated by $\Delta T$ based on the pitch of the optical interaction portions in waveguide 130 and the bandwidth of detector 152, as described above.

The output photons resulting from interactions with optical interaction portions in waveguide 130 exit back into coupler $160_2$ and are decoupled into two different predetermined wavelengths that are provided to separators $106_1$ and $106_2$, respectively. As discussed in more detail below with reference to FIGS. 9 to 11, separators $106_1$ and $106_2$ may direct photons of a particular wavelength in a first direction and photons of a different wavelength in a different direction, such as when using a dichroic mirror. In other implementations, separators $106_1$ and $106_2$ may direct photons of a predetermined wavelength in one direction when affected by a temporary condition, such as an acoustic wave, and direct photons of the predetermined wavelength in a different direction when no longer affected by the temporary condition. In yet other implementations, separators $106_1$ and $106_2$ may allow half the photons of any wavelength to pass through and reflect the other half of the photons out of the separator in a different direction, such as when the separators use a beam splitter.

In the example of FIG. 5B, separators $106_1$ and $106_2$ direct the photons into coupler $160_1$, which combines the two light paths into one light path that is input into detector 152. For its part, detector 152 converts the photons received from coupler $160_1$ into an electrical signal provided to analyzer 154, which determines relative locations of the optical interaction portions in waveguide 130 that indicate a match between the string of query symbols and the reference symbols represented by the optical interaction portions.

FIG. 5C depicts an arrangement of system 100 including a single waveguide 130 and detectors $152_1$ and $152_2$ according to one or more embodiments. As shown in FIG. 5C, a coupler between separators 106 and detectors 152 is not needed because there is a detector for each light path exiting separators 106. As with the example of FIG. 5B, waveguide 130 in FIG. 5C is fed photons from light sources $104_1$ and $104_2$ that are directed to coupler 160, which combines the light paths before the photons enter waveguide 130. Each of light sources $104_1$ and $104_2$ may emit photons of different predetermined wavelengths representing two different query symbols. The timing of the emission of the pulses of photons may be controlled by a controller (e.g., controller 102 in FIG. 1) to provide a reverse order of the string of query symbols separated from each other by ΔT based on the pitch of the optical interaction portions in waveguide 130 and the bandwidth of detectors 152, as described above.

The output photons resulting from interactions with optical interaction portions in waveguide 130 exit back into coupler 160 and are decoupled into two different predetermined wavelengths that are provided to separators $106_1$ and $106_2$, respectively. Separators $106_1$ and $106_2$ direct the photons into respective detectors $152_1$ and $152_2$. Detectors 152 convert the photons received from separators 106 into an electrical signal provided to analyzer 154, which determines relative locations of the optical interaction portions in waveguide 130 that indicate a match between the string of query symbols and the reference symbols represented by the optical interaction portions.

Those of ordinary skill in the art will appreciate with reference to the present disclosure that other arrangements of the devices depicted in FIGS. 5A to 5C are possible. For example, other implementations may include more light sources supplying photons of additional predetermined wavelengths representing additional query symbols.

Optical Interaction Portion Examples

FIG. 6 depicts an example of an optical interaction portion that is a nonreciprocal grating according to one or more embodiments. A nonreciprocal grating is asymmetric in that it reflects photons traveling in one direction but passes photons through that are traveling in the opposite direction. As shown by the arrows in FIG. 6, photons of predetermined wavelength Ai are reflected when reaching optical interaction portion $136_1$ from an entry side of waveguide 130 but photons of Ai are allowed to pass through optical interaction portion $136_1$ from the opposite direction. This property of optical interaction portion $136_1$ enables photons to return to the entry side of waveguide 130 for detection by detector 152.

Optical interaction portion $136_2$ in FIG. 6 provides additional detail on the construction of one type of nonreciprocal grating, a nonreciprocal Bragg grating on a chip. In this regard, waveguide 130 can be a planar waveguide in some implementations, as opposed to the examples of optical fiber waveguides discussed above for waveguides 130. As shown in FIG. 6, optical interaction portion $136_2$ includes silver stripe 140 on silica substrate 131 and alternating blocks of undoped Poly(methyl methacrylate) (PMMA), such as PMMA block $138_2$, and PMMA doped with infrared dye IR-140, such as doped PMMA block $138_1$.

The optical interaction portions can be tuned to reflect more photons of the predetermined wavelength the farther they are from the entry side of waveguide 130 to equalize the number of photons exiting from waveguide 130 for a match and to allow a certain fraction of input photons of the predetermined wavelength to continue to travel along waveguide 130 to interact with more optical interaction portions tuned to the predetermined wavelength.

Figure 7A:
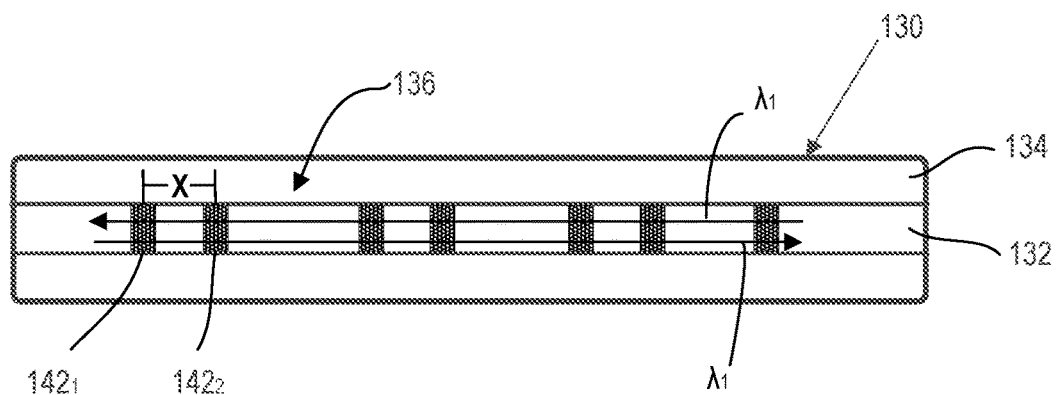
FIG. 7A depicts an acousto-optic grating in a waveguide in a transmission state according to one or more embodiments.

FIG. 7A depicts an example of an optical interaction portion that is an acousto-optic grating according to one or more embodiments. In FIG. 7A, optical interaction portion 136 is in an unaligned or transmission state where the distance x between interference portions $142_1$ and $142_2$ in core 132 of waveguide 130 allows for photons of wavelength Ai to pass through optical interaction portion 136.

Figure 7B:
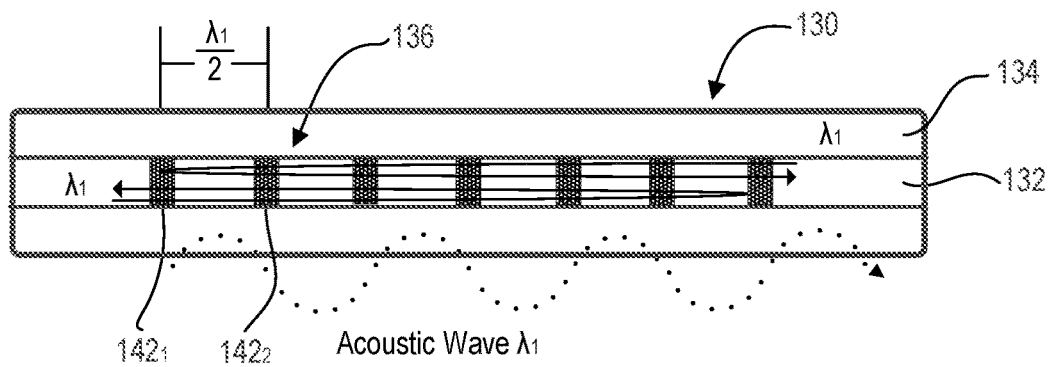
FIG. 7B depicts the acousto-optic grating of FIG. 7A in a reflection state according to one or more embodiments.

In FIG. 7B, optical interaction portion 136 is excited by an acoustic wave with a wavelength of Ai that temporarily changes the spacing between interference portions $142_1$ and $142_2$ in core 132 of waveguide 130. As shown in FIG. 7B, the spacing between interference portions $142_1$ and $142_2$ changes to $\lambda_1/2$, which puts optical interaction portion 136 into a reflection state where photons of wavelength Ai are reflected. As with other optical interaction portions discussed above, optical interaction portion 136 in FIG. 7B only reflects photons of the predetermined wavelength $\lambda_1$ corresponding to a particular reference symbol.

After the acoustic wave passes, optical interaction portion 136 returns to its unaligned or transmission state to allow photons of different wavelengths, including the predetermined wavelength $\lambda_1$, to pass through optical interaction portion 136. As noted above, the optical interaction portions can be tuned to reflect more photons of the predetermined wavelength the farther they are from the entry side of waveguide 130 to more closely equalize the number of photons exiting from waveguide 130 for a match and to allow a certain fraction of photons of the predetermined wavelength to continue to travel down waveguide 130 to interact with more optical interaction portions tuned to the predetermined wavelength.

The acoustic wave propagated along waveguide 130 may travel primarily in a coating and/or cladding 134 of waveguide 130. In some implementations, a controller for the system (e.g., controller 102 in FIG. 1) can continuously emit photons of a predetermined wavelength from a light source for a longer time, as opposed to the shorter pulses of photons discussed above. The controller then controls an acoustic wave generator (e.g., acoustic wave generator(s) 150 in FIG. 1) to generate an acoustic wave with the same predetermined wavelength as the photons emitted from the light source so that the photons at the optical interaction portions for the predetermined wavelength temporarily reflect the photons as the acoustic wave propagates along the waveguide. Such an arrangement will operate at the speed of sound when passing through the material of coating and/or cladding 134.

In some cases, wave dispersion or the change in the length of the acoustic wave as the wave propagates farther along the waveguide may limit the length of the waveguide. In such cases, the reference sequence can be broken into shorter waveguides, as in the example of FIG. 3A. In addition, the photons of different predetermined wavelengths for different query symbols can be continuously sent into different waveguides (i.e., longer pulses) and acoustic waves of the corresponding predetermined wavelengths can be generated for propagation along their respective waveguide one at a time with appropriate delays between the acoustic waves so that the output photons are temporally aligned. The timing of the delays or staggering of the acoustic waves can be based on the pitch between the acousto-optic gratings and/or the bandwidth of the detector or detectors.

Figure 8:
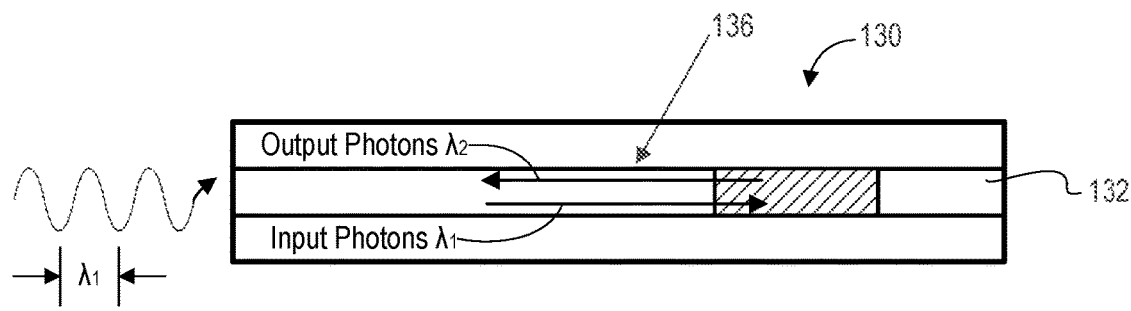
FIG. 8 depicts a luminescent material portion in a waveguide according to one or more embodiments.

FIG. 8 depicts an example of an optical interaction portion that is a luminescent material portion in waveguide 130 according to one or more embodiments. As shown in FIG. 8, input photons of wavelength $\lambda i$ reach optical interaction portion 136 in core 132 of waveguide 130 and match the absorption spectrum of the luminescent material causing the luminescent material to emit output photons of a second predetermined wavelength of $\lambda_2$.

In some implementations, the luminescent material portions may be added to waveguide 130 by, for example, injecting a beam of ions of the luminescent material into core 132. The luminescent material can include, for example, lanthanides that have different absorption spectrums corresponding to the different predetermined wavelengths used for the query symbols.

Those of ordinary skill in the art will appreciate with reference to the present disclosure that some systems may include a combination of different types of optical interaction portions that may provide for detection of a wider range of different wavelengths. For example, a first predetermined wavelength for input photons may be used for input into a first waveguide that may have nonreciprocal gratings for optical interaction portions, while a second predetermined wavelength for input photons may be used for input into a second waveguide that may have luminescent material portions for optical interaction portions.

Separator Examples

Figure 9:
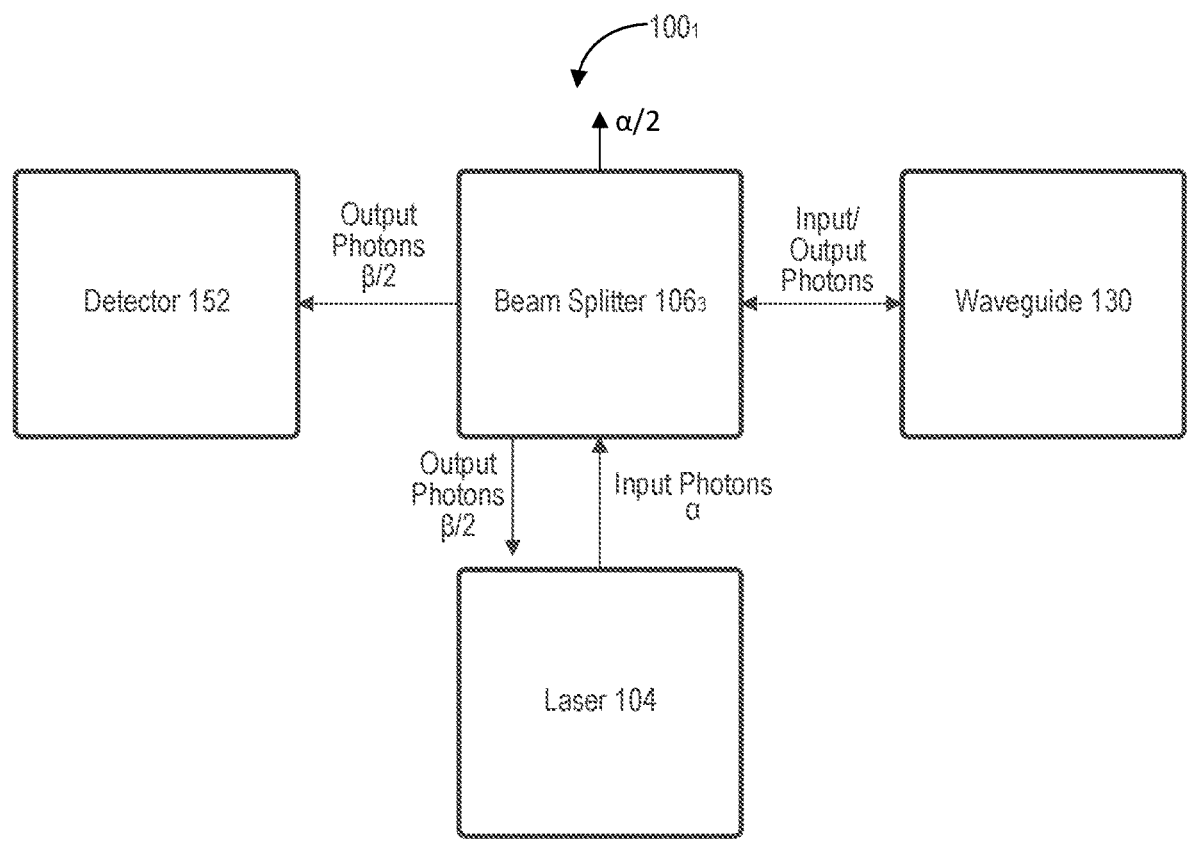
FIG. 9 depicts an arrangement of a system including a beam splitter according to one or embodiments.

FIG. 9 depicts an arrangement of system $100_1$ including beam splitter $106_3$ as a separator according to one or more embodiments. As shown in FIG. 9, system $100_1$ includes laser 104 as a light source to emit input photons a into beam splitter $106_3$. Half of the input photons are reflected into waveguide 130 and the other half of the input photons (i.e., $\alpha/2$ in FIG. 9) are transmitted through beam splitter $106_3$ and are lost from system $100_1$.

A portion of the input photons that reach waveguide 130 are reflected out of waveguide 130 as output photons back to beam splitter $106_3$. Half of the output photons pass through beam splitter $106_3$ (342 in FIG. 9) to detector 152 and the other half of the output photons ($\beta/2$) are reflected toward laser 104 and are not detected. The amount of input photons supplied by laser 104 therefore needs to be great enough to allow for the detection of matching optical interaction portions in waveguide 130 given the sensitivity of detector 152 and the losses of input photons and output photons at beam splitter $106_3$.

Figure 10:
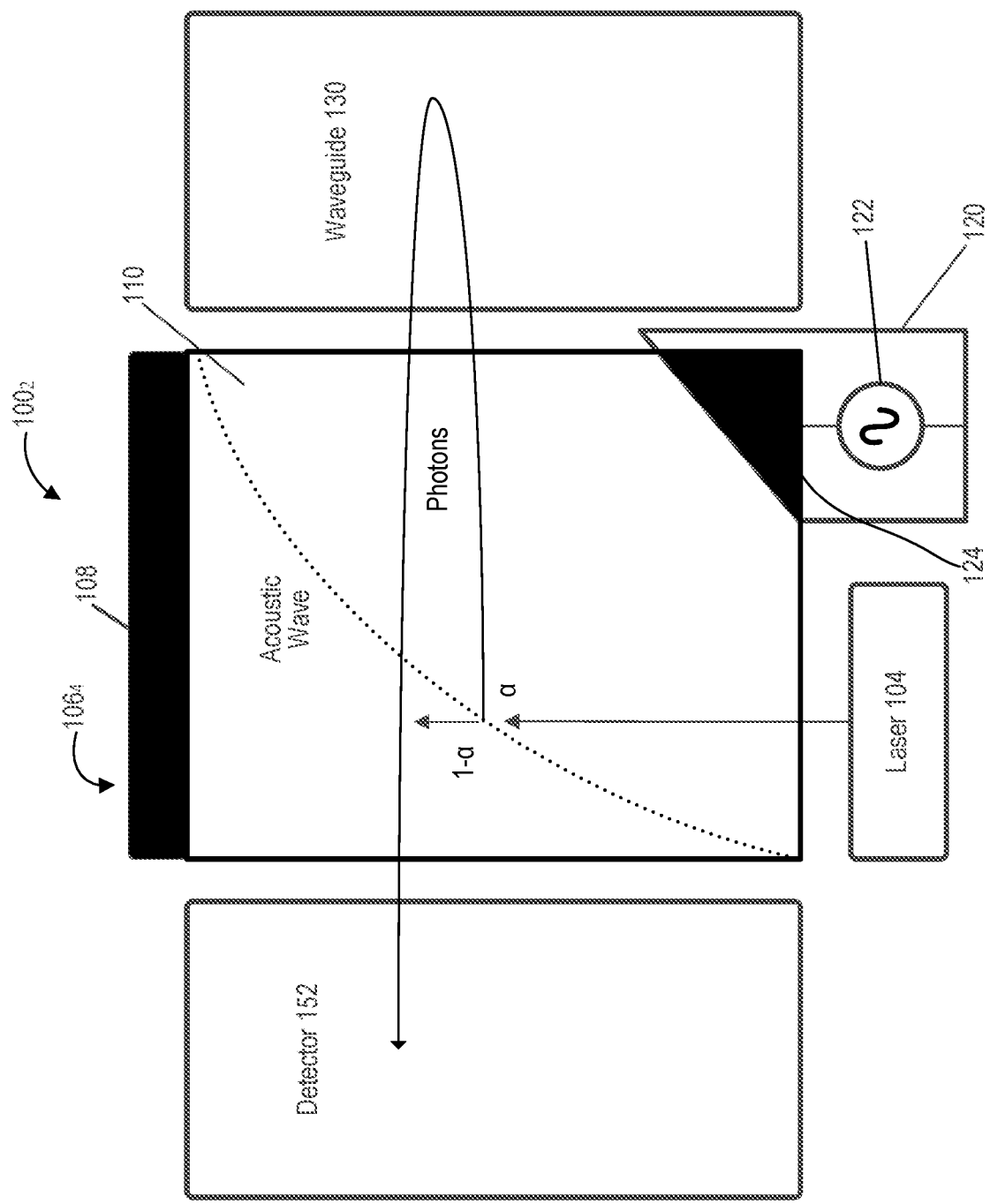
FIG. 10 depicts an arrangement of a system including an acousto-optic deflector according to one or more embodiments.

FIG. 10 depicts an arrangement of system 1002 including acousto-optic deflector $106_4$ as a separator according to one or more embodiments. As shown in FIG. 10, system 1002 includes laser 104 as a light source to emit input photons into acousto-optic deflector $106_4$. A fraction of the input photons shown as a in FIG. 10 are reflected into waveguide 130 and the remaining input photons or ($1-\alpha$) of the input photons are transmitted through body 110 of acousto-optic deflector $106_4$ and are lost from system $100_1$.

Body 110 of acousto-optic deflector $106_4$ can include, for example, a quartz crystal such that an acoustic wave generated by acoustic wave generator 120 travels through body 110 to temporarily change the structure of body 110 to reflect more input photons toward waveguide 130 (i.e., increase $\alpha$). This can increase the number of input photons entering waveguide 130. Acoustic wave generator 120 in the example of FIG. 1, includes a driver or amplifier 122 that causes transducer 124, which is in contact with body 110, to generate the acoustic wave. The frequency or wavelength of the acoustic wave may be tuned specifically to the material used for body 110 to create the greatest amount of reflection of the input photons of a predetermined wavelength (i.e., to increase $\alpha$).

After the acoustic wave has been absorbed by acoustic absorber 108, body 110 of acousto-optic deflector $106_4$ can allow most of the output photons returning from waveguide 130 to pass through acousto-optic deflector $106_4$ to enable more output photons to be detected by detector 152 as compared to using a beam splitter as in FIG. 9, which can improve detection or allow for less input photons to be emitted by laser 104, a longer waveguide with more optical interaction portions, and/or a less sensitive detector.

Figure 11:
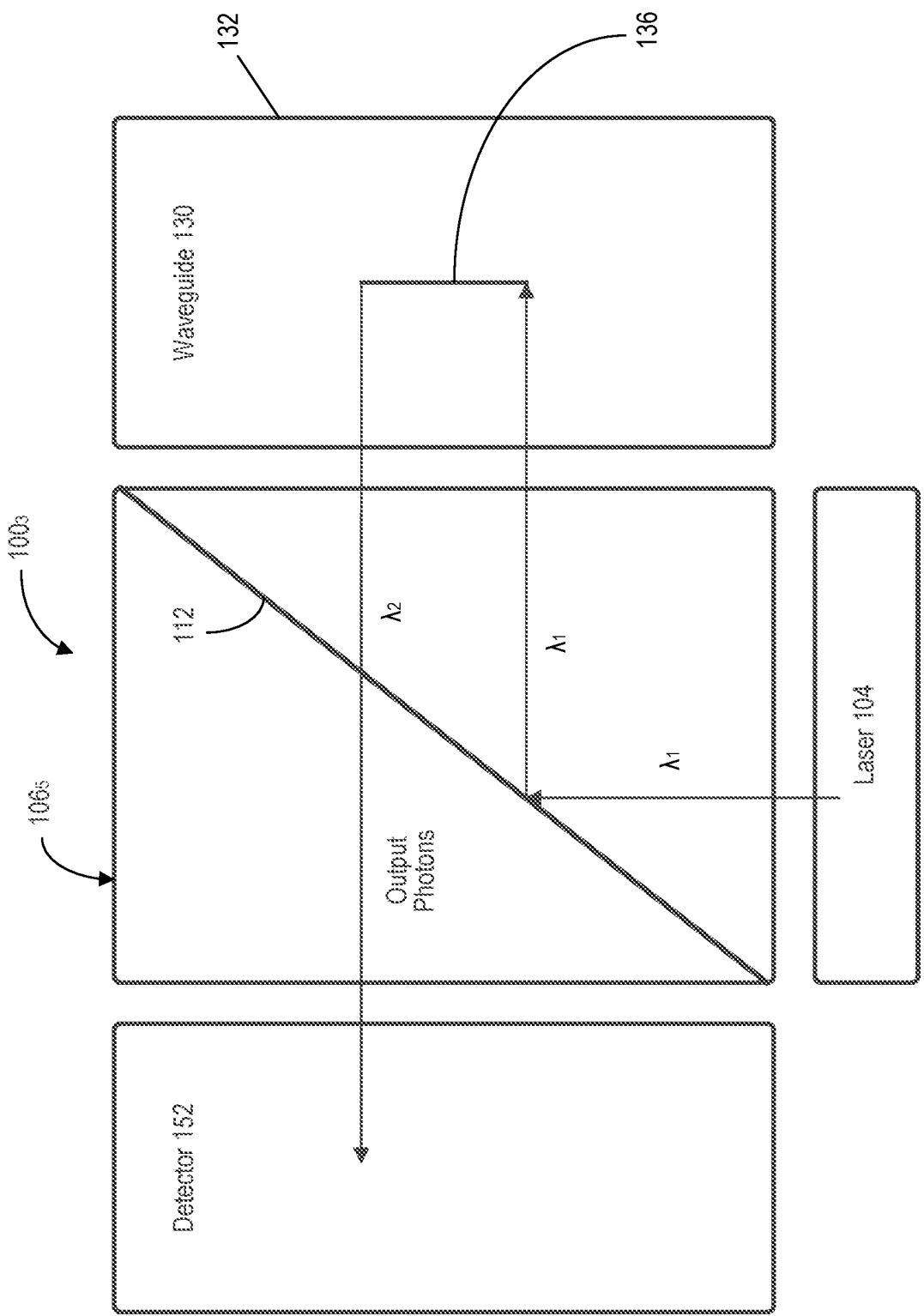
FIG. 11 depicts an arrangement of a system including a dichroic mirror according to one or more embodiments.

FIG. 11 depicts an arrangement of a system including dichroic mirror $106_5$ as a separator according to one or more embodiments. As shown in FIG. 11, system 1003 includes laser 104 as a light source to emit input photons of a first predetermined wavelength $\lambda i$ into dichroic mirror $106_5$. The input photons are reflected by layer 112 out of dichroic mirror $106_5$ into waveguide 130 where the input photons are reflected by optical interaction portion 136, which includes a luminescent material. Output photons of a second predetermined wavelength $\lambda_2$ are emitted from optical interaction portion 136 because of the interaction with the luminescent material. The output photons of the second predetermined wavelength $\lambda_2$ are transmitted through dichroic mirror $106_5$, without being reflected by layer 112.

The use of a dichroic mirror in implementations where luminescent materials are used for optical interaction portions 136 can enable more input photons to reach waveguide 130 as compared to using a beam splitter for a separator. In addition, a greater proportion of output photons of the second predetermined wavelength reach detector 152 as compared to the proportion of output photons that reach the detector in systems using a beam splitter as a separator. As noted above for the example of an acousto-optic deflector in FIG. 10, more output photons reaching the detector can improve detection or allow for less input photons to be emitted by laser 104, a longer waveguide with more optical interaction portions, and/or a less sensitive detector.

Those of ordinary skill in the art will appreciate with reference to the present disclosure that the arrangements shown in FIGS. 5A to 5C are for illustration purposes and that actual systems may include additional detectors, separators, light sources, waveguides, and optical interaction portions.

Query Symbol Locating Examples

Figure 12:
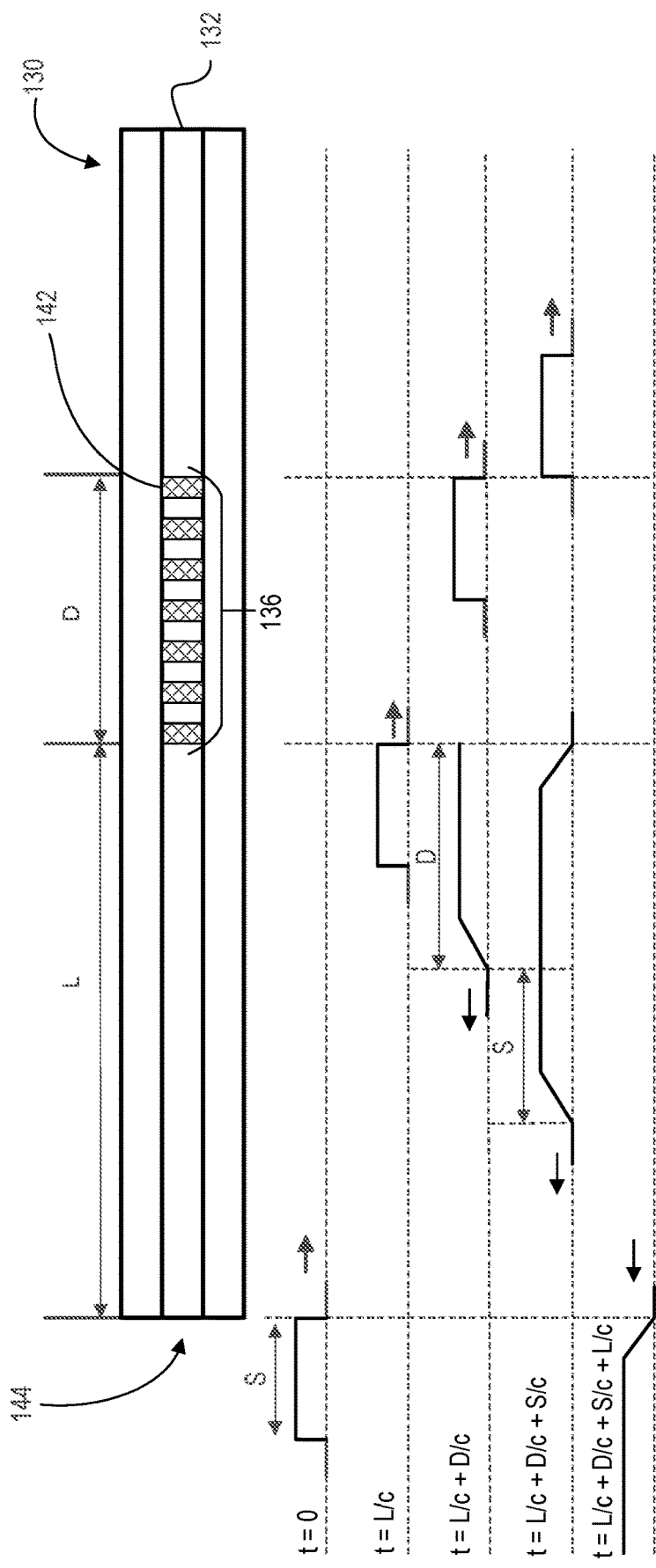
FIG. 12 illustrates the calculation of a difference in time between photons being sent into a waveguide and detection of a peak level of photons according to one or more embodiments.

FIG. 12 illustrates the calculation of a difference in time between photons being sent into waveguide 130 and detection of a peak level of photons according to one or more embodiments. The detection of the peak level of photons (e.g., greater than or equal to a threshold number of photons) can correspond to a match between a query symbol and a reference symbol represented by optical interaction portion 136 in waveguide 130. The time between when the input photons enter waveguide 130 at entry side 144 and when the output photons are detected corresponds to the relative location of optical interaction portion 136 in waveguide 130 with respect to other optical interaction portions. As a result, the relative location of the matching reference symbol among the reference symbols in the reference sequence can be determined based on the travel time of the photons.

As shown in FIG. 12, different times are shown on the left in the top two sections for the location of a pulse of input photons as it travels to the right into waveguide 130 from entry side 144 through core 132 and into optical interaction portion 136. At time t=0 shown in the top section, the pulse of input photons reaches entry side 144 of waveguide 130. The distances between light sources, waveguides, and detectors, the slowing of photons traveling through any separators or couplers, and any detection delay caused by a detector can remain set at equal distances or delays that provide the same baseline system delay for different pulses of input photons. This baseline system delay therefore does not affect the relative photon travel times for different pulses of input photons if the baseline system delay remains the same for the different pulses of input photons.

At time t=L/c shown in the next section below, the pulse reaches the beginning of optical interaction portion 136 in core 132. In this equation, L is the distance from entry side 144 to the beginning of optical interaction portion 136 and c is the speed of light in core 132, which is reduced or scaled down from the speed of light in a vacuum to account for the refractive index of the material in core 132 and the changes in material at the optical interaction portions.

At time t=L/c+D/c shown in the next section below, a pulse of output photons results from an optical interaction between optical interaction portion 136 and the pulse of input photons and at least a portion of the pulse of input photons continues to travel away from entry side 144 through core 132. In some implementations, the optical interaction can include a portion of the input photons being reflected back towards entry side 144 and a remaining portion of the input photons passing through optical interaction portion 136. The distance D is the distance of the optical interaction portion. In the example of FIG. 12, D is the distance between a first interference portion and a last interference portion 142 of optical interaction portion 136.

At time t=L/c+D/c+S/c shown in the next section below, the output photons have completely left optical interaction portion 136. The distance S is the length of the pulse of photons. The total length from the first output photon to the last output photon leaving optical interaction portion 136 is within a distance of S+D. At time t=L/c+D/c+S/c+L/c in the next section below, the last output photon has left entry side 144 of waveguide 130. In this regard, the total length of the space occupied by the output photons in the example of FIG. 12 is the length of the pulse of input photons S plus the length of optical interaction portion D. In some implementations, the distance S can be less than the distance D of the length of the optical interaction portions in waveguide 130 to aid in the detection of discrete groups of output photons representing different optical interaction portions. For example, the distance S of the pulse of input photons may be 7 micrometers and the distance D of the optical interaction portions can be 10 micrometers. In other implementations where an acoustic wave is used to change acousto-optic gratings into a reflective state, the pulse of input photons can be much longer than D because the timing and duration of the reflected output photons is determined by the duration of the acoustic wave as it propagates along the optical interaction portions.

In some implementations, the detection of the peak level of output photons detected by a detector may occur near the middle of the pulse of output photons. In such cases, the time from the pulse of input photons entering waveguide 130 and the middle of the pulse of output photons to be detected can be represented as shown below in Equation 2:

$$t = \frac{L}{c} + \frac{D}{c} + \frac{S}{c} + \frac{L}{c} - \frac{D+S}{2c} \qquad \text{Eq. 2}$$

where c is the speed of light in the waveguide, L is the length from the entry side of the waveguide to the optical interaction portion, D is the length of the optical interaction portion, and S is the length of the pulse of input photons.

When a series of pulses of different predetermined wavelengths is input into the waveguide to represent a string of query symbols, the relative location of the query string in the reference sequence can be determined by measuring the photon travel time for the first pulse of photons. With reference to the example of FIG. 2D, the groups of output photons identified by boxes $12_A$ and $12_B$ are the peak levels of photons that are greater than a threshold level of photons set at the detector. The threshold level can be set based on the number of pulses or query symbols input into the waveguide, the duration of the pulses, and characteristics of the waveguide(s), such as the number and type of optical interaction portions. Preferably, the optical interaction portions in the waveguide(s) are tuned to return approximately the same number of output photons for a matching predetermined wavelength by increasing the number of output photons returned as the optical interaction portions get farther from the entry side of the waveguide(s).

The analyzer can use the time of detection determined from a signal received from the detector and the time when the first pulse was emitted from the light source to determine L indicating the distance into the waveguide where the matching optical interaction portion is located, as discussed in more detail below for FIG. 13. The photon travel time for the string of query symbols can be represented by the time from the first pulse of photons entering the waveguide until the middle of the last pulse of output photons leaves the waveguide, which results from the optical interaction of the first pulse of input photons. This photon travel time for the query string can be represented as shown in Equation 3 below:

$$t = \Delta T(Q-1) + \frac{L}{c} + \frac{D}{c} + \frac{S}{c} + \frac{L}{c} - \frac{D+S}{2c} \qquad \text{Eq. 3}$$

where ΔT is the time interval between the pulses of different predetermined wavelengths as discussed above with reference to Equation 1 and Q is the total number of query symbols. In some implementations, the detector may sum photons that are detected within a sliding window of QΔT and matches of the query string are indicated by a detected number of photons that are approximately Q times an average or expected number of output photons resulting from a matching optical interaction portion.

Figure 13:
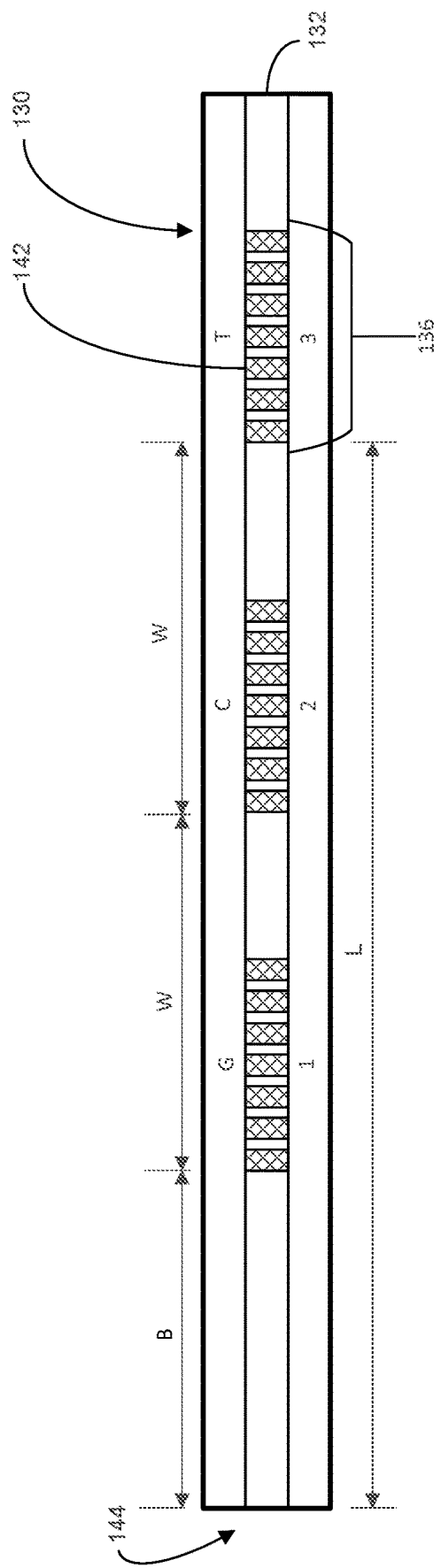
FIG. 13 illustrates the determination of a relative location of an optical interaction portion according to one or more embodiments.

FIG. 13 illustrates the determination of a relative location of an optical interaction portion according to one or more embodiments. As shown in FIG. 13, each optical interaction portion 136 in core 132 shown in waveguide 130 has an index indicating its relative location among the other optical interaction portions (i.e., indices 1, 2, and 3 in FIG. 13). The distance $L_i$ for a given optical interaction portion from entry side 144 can be represented in terms of its index, i, as shown in Equation 4 below:

$$L_i = B + W(i-1) \qquad \text{Eq. 4}$$

where B is a buffer distance from entry side 144 to the first optical interaction portion with index i=1, and W is the pitch between the optical interaction portions (i.e., the distance between the start of a first optical interaction portions to the start of the next optical interaction portion).

Substituting Li from Equation 4 into Equation 3 to provide t, which is the photon travel time to and from the optical interaction portion with index i, results in Equation 5 below.

$$t_i = \Delta T(Q-1) + \frac{2L_i}{c} + \frac{D+S}{2c} \qquad \text{Eq. 5}$$

From the time t of peak photon detection, the index of the matching optical interaction portion, i, can be calculated with Equation 6 below.

$$i = 1 + \frac{1}{W}\left\{\left[t_i - \Delta T(Q-1) - \frac{D+S}{2c}\right]\right\}\frac{C}{2} - B \qquad \text{Eq. 6}$$

In some implementations, the analyzer of the system can calculate the index based on a time it receives a signal from a detector indicating a peak photon level from when a light source sent input photons into the waveguide. The index can then be used to indicate the relative location of one or more query symbols (e.g., a query string) within the reference sequence represented by the optical interaction portions of the waveguide.

Figure 14:
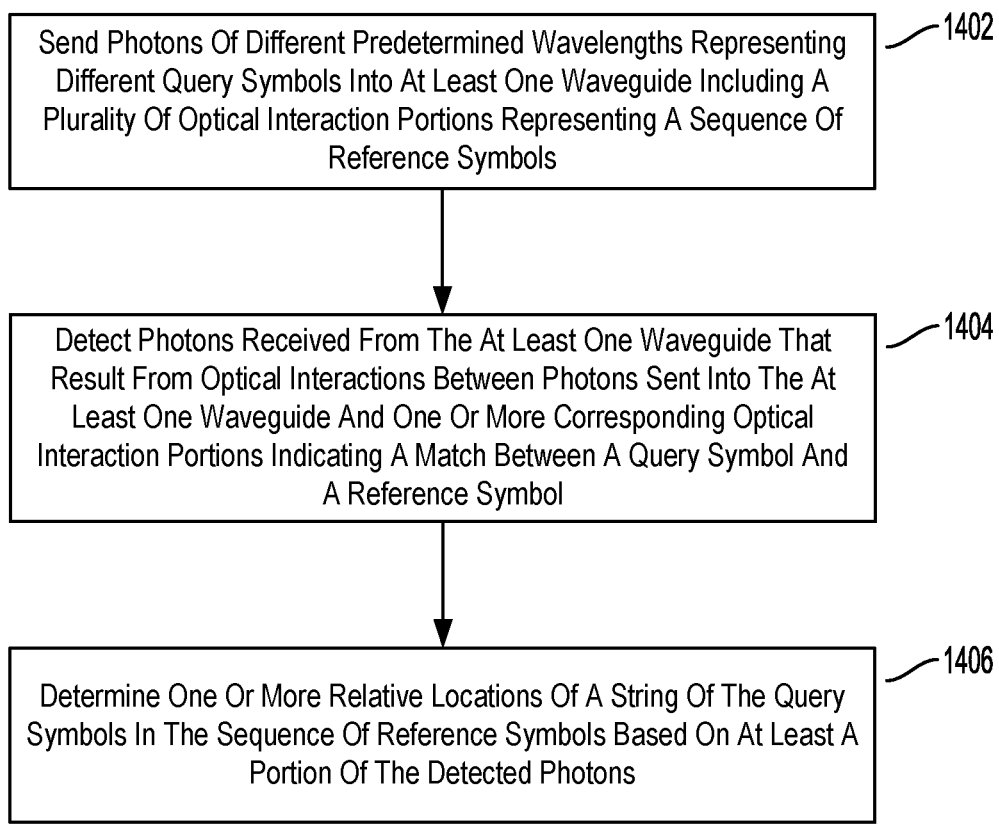
FIG. 14 is a flowchart for a query symbol locating process according to one or more embodiments.

FIG. 14 is a flowchart for a query symbol locating process according to one or more embodiments. The process of FIG. 14 can be performed by, for example, system 100 in FIG. 1 with certain components of the system, such as light sources 104 and analyzer 154 being controlled by controller 102 executing application 10.

In block 1402, one or more light sources are controlled to send input photons of different predetermined wavelengths from a set of predetermined wavelengths representing different respective query symbols into at least one waveguide. The input photons can include, for example, visible light, infrared light, and/or ultraviolet light. In some implementations, the input photons of the different predetermined wavelengths can be sent into one or more waveguides in a staggered pattern or time delayed pattern to temporally align output photons from the one or more waveguides. In such implementations, the input photons of the different predetermined wavelengths can be sent in a reverse order with respect to the corresponding query symbols of the query string to facilitate the alignment of the output photons indicating a match. As discussed above, each waveguide includes a plurality of optical interaction portions that each represent a different reference symbol, and collectively represent a sequence of reference symbols. Each optical interaction portion is configured to optically interact with input photons of a predetermined wavelength of the set of different predetermined wavelengths, and not to optically interact, or minimally interact with photons of other predetermined wavelengths in the set of different predetermined wavelengths.

The optical interaction portions can include, for example, nonreciprocal gratings, such as nonreciprocal Bragg gratings, that have been tuned to reflect a portion of the photons having the corresponding predetermined wavelength. In some cases, the tuning of the nonreciprocal grating may temporarily occur as an acoustic wave reaches the optical interaction portion, as discussed above with reference to FIGS. 7A and 7B. In yet other implementations, the optical interaction portions can include, for example, luminescent material portions that emit output photons of another predetermined wavelength when excited by input photons of the corresponding predetermined wavelength from the set of predetermined wavelengths for input photons. Such luminescent material portions can include, for example, lanthanide materials, as discussed above with reference to FIG. 8.

In block 1404, a detector detects output photons received from the at least one waveguide that result from optical interactions between the input photons sent into the at least one waveguide and one or more corresponding optical interaction portions. The detected output photons represent a match between a query symbol and a reference symbol in the sequence of reference symbols. As discussed above, the detector may include, for example, an avalanche photodetector that can count or represent a number of photons received at a particular time or window of time with an electrical signal, such as a voltage output.

In block 1406, one or more relative locations are determined for a string of query symbols within the sequence of reference symbols based on at least a portion of the photons detected in block 1404. As discussed above with reference to FIGS. 12 and 13, the determination of the one or more relative locations can be based on a difference in time that is calculated between when the input photons are sent into the waveguide and when a peak level of the output photons are detected. This photon travel time can be used to derive an index in some implementations for a relative starting position of the matching reference symbols in the sequence of reference symbols.

As discussed above, the foregoing optical systems and methods for locating query symbols in a reference sequence can significantly improve computing efficiency and simplify the computations, as compared to conventional systems due in part to moving at least some of the computation and/or data storage into an optical domain. As a result, the foregoing systems and methods can identify matching sequences or query symbols faster than conventional systems that may rely on large amounts of memory and processing resources. In addition to time savings, the power consumption and cost of the foregoing optical systems may be reduced as compared to conventional systems that use large amounts of volatile memory to perform different phases of exact matching and/or approximate matching.

OTHER EMBODIMENTS

Those of ordinary skill in the art will appreciate that the various illustrative logical blocks, modules, and processes described in connection with the examples disclosed herein may be implemented as electronic hardware, software, or combinations of both. Furthermore, the foregoing processes can be embodied on a computer readable medium which causes a processor, controller, or other circuitry to perform or execute certain functions.

To clearly illustrate this interchangeability of hardware and software, various illustrative components, blocks, and modules have been described above generally in terms of their functionality. Whether such functionality is implemented as hardware or software depends upon the particular application and design constraints imposed on the overall system. Those of ordinary skill in the art may implement the described functionality in varying ways for each particular application, but such implementation decisions should not be interpreted as causing a departure from the scope of the present disclosure.

The various illustrative logical blocks, units, modules, and circuitry described in connection with the examples disclosed herein may be implemented or performed with a general-purpose processor, a GPU, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. Processor or controller circuitry may also be implemented as a combination of computing devices, e.g., a combination of a DSP and a microprocessor, a plurality of microprocessors, an SoC, one or more microprocessors in conjunction with a DSP core, or any other such configuration.

The activities of a method or process described in connection with the examples disclosed herein may be embodied directly in hardware, in a software module executed by processor or other circuitry, or in a combination of the two. The steps of the method or algorithm may also be performed in an alternate order from those provided in the examples. A software module may reside in RAM memory, flash memory, ROM memory, EPROM memory, EEPROM memory, registers, hard disk, a removable media, an optical media, or any other form of storage medium known in the art. An exemplary storage medium is coupled to processor or controller circuitry such that the processor or controller circuitry can read information from, and write information to, the storage medium. In the alternative, the storage medium may be integral to processor or controller circuitry. The processor or controller circuitry and the storage medium may reside in an ASIC or an SoC.

The foregoing description of the disclosed example embodiments is provided to enable any person of ordinary skill in the art to make or use the embodiments in the present disclosure. Various modifications to these examples will be readily apparent to those of ordinary skill in the art, and the principles disclosed herein may be applied to other examples without departing from the spirit or scope of the present disclosure. The described embodiments are to be considered in all respects only as illustrative and not restrictive. In addition, the use of language in the form of "at least one of A and B" in the following claims should be understood to mean "only A, only B, or both A and B."

What is claimed is:

1. A system, comprising:
    a waveguide including a plurality of optical interaction portions, wherein each optical interaction portion of the plurality of optical interaction portions represents a reference symbol in a reference sequence and a relative location of the optical interaction portion in the waveguide is based on a corresponding relative location of the reference symbol in the reference sequence;
    at least one light source configured to send photons of a predetermined wavelength into the waveguide, wherein the predetermined wavelength represents a query symbol;
    a detector configured to detect photons received from the at least one waveguide, wherein the received photons detected by the detector result from optical interactions between photons sent into the waveguide by the at least one light source and one or more corresponding optical interaction portions of the plurality of optical interaction portions, and wherein an optical interaction between photons of the predetermined wavelength and an optical interaction portion indicates a match between the query symbol and the reference symbol in the reference sequence; and
    an analyzer configured to determine one or more respective relative locations of the one or more corresponding optical interaction portions in the waveguide that optically interact with photons of the predetermined wavelength indicating one or more relative locations of the query symbol in the reference sequence.

2. The system of claim 1, wherein the analyzer is further configured to determine one or more indices for the one or more respective relative locations based on a difference in time between photons being sent into the waveguide and detection of a peak level of photons detected by the detector.

3. The system of claim 1, wherein the plurality of optical interaction portions includes a plurality of nonreciprocal gratings.

4. The system of claim 3, wherein nonreciprocal gratings of the plurality of nonreciprocal gratings are tuned to reflect increasing amounts of photons the farther the nonreciprocal gratings are located from an entry side of the waveguide where the photons of the predetermined wavelength enter the waveguide.

5. The system of claim 1, further comprising:
    an acoustic wave generator configured to propagate an acoustic wave along the waveguide; and
    wherein the plurality of optical interaction portions includes a plurality of gratings configured to form a temporary reflective grating when excited by the acoustic wave.

6. The system of claim 1, wherein the plurality of optical interaction portions includes a plurality of luminescent material portions in the waveguide.

7. The system of claim 1, further comprising a dichroic deflector on an entry side of the waveguide where the photons of the predetermined wavelength enter the waveguide, wherein the dichroic deflector is configured to reflect either photons of the predetermined wavelength or photons of a different wavelength emitted from the corresponding one or more optical interaction portions.

8. The system of claim 1, further comprising an additional waveguide including an additional plurality of optical interaction portions, wherein each of the additional optical interaction portions of the additional plurality of optical interaction portions represents a reference symbol in the reference sequence and a relative location of the additional optical interaction portion in the additional waveguide is based on a corresponding relative location of the reference symbol in the reference sequence.

9. The system of claim 8, wherein the at least one light source is further configured to send photons of a different predetermined wavelength representing a different query symbol into the additional waveguide.

10. The system of claim 1, wherein the at least one light source is further configured to stagger sending photons of different predetermined wavelengths representing different query symbols such that the order of staggering the sending of the photons of the different predetermined wavelengths represents a reverse order of query symbols in a string of query symbols.

11. The system of claim 1, wherein the photons sent into the waveguide comprise at least one of visible light, infrared light, and ultraviolet light.

12. The system of claim 1, further comprising:
an acoustic wave generator configured to generate an acoustic wave; and
an acousto-optic deflector in contact with the acoustic wave generator and on an entry side of the waveguide where the photons of the predetermined wavelength enter the waveguide, wherein the acousto-optic deflector is configured to reflect photons of the predetermined wavelength as the generated acoustic wave passes through the acousto-optic deflector and not reflect photons of the predetermined wavelength when the generated acoustic wave is not passing through the acousto-optic deflector.

13. A method, comprising:
sending photons of different predetermined wavelengths representing different respective query symbols into at least one waveguide, wherein the at least one waveguide includes a plurality of optical interaction portions with each of the optical interaction portions representing a reference symbol by optically interacting with photons of a corresponding predetermined wavelength and the plurality of optical interaction portions representing a sequence of the reference symbols based on the order of the plurality of optical interaction portions in the at least one waveguide;
detecting photons received from the at least one waveguide, wherein the received photons result from optical interactions between photons sent into the at least one waveguide and one or more corresponding optical interaction portions of the plurality of optical interaction portions, and wherein an optical interaction between photons of a predetermined wavelength and an optical interaction portion indicates a match between a query symbol and a reference symbol; and
based on at least a portion of the detected photons, determining one or more relative locations of a string of the query symbols in the reference sequence.

14. The method of claim 13, further comprising determining the one or more relative locations based on a difference in time between photons being sent into the at least one waveguide and detection of a peak level of photons.

15. The method of claim 13, further comprising propagating an acoustic wave along a waveguide of the at least one waveguide, wherein the plurality of optical interaction portions includes a plurality of gratings configured to form a temporary reflective grating when excited by the propagated acoustic wave.

16. The method of claim 13, wherein the plurality of optical interaction portions includes a plurality of luminescent material portions in the at least one waveguide.

17. The method of claim 13, further comprising using a dichroic deflector on an entry side of a waveguide of the at least one waveguide where the photons enter the waveguide to reflect either photons of a predetermined wavelength or photons of a different wavelength emitted from the corresponding one or more optical interaction portions.

18. The method of claim 13, further comprising staggering the sending of the photons based on their different predetermined wavelengths such that the order of staggering represents a reverse order of the string of query symbols.

19. The method of claim 13, further comprising:
propagating an acoustic wave into an acousto-optic deflector on an entry side of a waveguide of the at least one waveguide where photons enter the waveguide such that photons of a first predetermined wavelength are reflected as the propagated acoustic wave passes through the acousto-optic deflector and photons of the first predetermined wavelength are transmitted through the acousto-optic deflector after the acoustic wave has passed through the acousto-optic deflector.

20. A system, comprising:
at least one waveguide including a plurality of optical interaction portions with each of the optical interaction portions representing a reference symbol by optically interacting with photons of a corresponding predetermined wavelength and the plurality of optical interaction portions representing a sequence of the reference symbols based on the order of the plurality of optical interaction portions in the at least one waveguide;
at least one light source configured to send photons of different predetermined wavelengths representing different respective query symbols into the at least one waveguide;
means for detecting photons received from the at least one waveguide, wherein the received photons result from optical interactions between photons sent into the at least one waveguide and one or more corresponding optical interaction portions of the plurality of optical interaction portions, and wherein an optical interaction between photons of a predetermined wavelength and an optical interaction portion indicates a match between a query symbol and a reference symbol; and
means for determining one or more relative locations of a string of the query symbols in the reference sequence based on at least a portion of the detected photons.

* * * * *